(12) United States Patent
Rezach

(10) Patent No.: US 11,903,617 B1
(45) Date of Patent: Feb. 20, 2024

(54) SPINAL IMPLANT SYSTEM AND METHODS OF USE

(71) Applicant: Warsaw Orthopedic, Inc., Warsaw, IN (US)

(72) Inventor: William Alan Rezach, Covington, TN (US)

(73) Assignee: Warsaw Orthopedic, Inc, Warsaw, IN (US)

(*) Notice: Subject to any disclaimer, the term of this patent is extended or adjusted under 35 U.S.C. 154(b) by 0 days.

(21) Appl. No.: 17/903,460

(22) Filed: Sep. 6, 2022

(51) Int. Cl.
*A61B 17/70* (2006.01)
*A61B 17/86* (2006.01)

(52) U.S. Cl.
CPC ...... *A61B 17/7032* (2013.01); *A61B 17/8605* (2013.01); *A61B 17/8685* (2013.01)

(58) Field of Classification Search
CPC ............ A61B 17/7032; A61B 17/8605; A61B 17/8685
USPC ....... 606/266, 267, 268, 269, 272, 277, 305, 606/308, 315, 316, 317, 319, 324, 328, 606/99, 104, 86 A
See application file for complete search history.

(56) References Cited

U.S. PATENT DOCUMENTS

| | | | |
|---|---|---|---|
| 5,683,392 A | 11/1997 | Richelsoph et al. | |
| 6,132,434 A | 10/2000 | Sherman et al. | |
| 7,503,924 B2 | 3/2009 | Lee et al. | |
| 7,988,694 B2 | 8/2011 | Barrus et al. | |
| 8,034,086 B2 | 10/2011 | Iott et al. | |
| 8,038,701 B2 | 10/2011 | Rock et al. | |
| 8,100,947 B2 | 1/2012 | Ensign et al. | |
| 8,162,991 B2 | 4/2012 | Strauss et al. | |
| 8,287,576 B2 | 10/2012 | Barrus | |
| 8,328,817 B2 | 12/2012 | Strauss | |
| 8,361,122 B2 | 1/2013 | Barrus et al. | |
| 8,617,217 B2 | 12/2013 | Iott et al. | |
| 8,790,374 B2 | 7/2014 | Iott et al. | |
| 8,814,919 B2 | 8/2014 | Barrus et al. | |
| 8,894,691 B2 | 11/2014 | Iott et al. | |
| 8,945,189 B2 | 2/2015 | Barrus et al. | |
| 9,247,969 B2 | 2/2016 | Nunley et al. | |
| 9,259,254 B2 | 2/2016 | Iott et al. | |
| 9,421,038 B2 | 8/2016 | Noordeen et al. | |
| 9,480,517 B2 * | 11/2016 | Jackson ............. | A61B 17/7082 |
| 9,532,816 B2 | 1/2017 | Barrus et al. | |
| 9,615,868 B2 * | 4/2017 | Butler ................ | A61B 17/7037 |
| 9,649,135 B2 * | 5/2017 | Doubler ............ | A61B 17/7049 |
| 9,655,664 B2 | 5/2017 | Barrus et al. | |
| 10,194,951 B2 * | 2/2019 | Jackson ............. | A61B 17/7037 |
| 10,285,735 B2 | 5/2019 | Barrus et al. | |
| 10,292,736 B2 | 5/2019 | Barrus et al. | |
| 10,722,271 B2 | 7/2020 | Barrus | |
| 10,722,276 B2 * | 7/2020 | Barrus ............... | A61B 17/7032 |
| 10,918,419 B2 | 2/2021 | Kishan et al. | |

(Continued)

*Primary Examiner* — Eduardo C Robert
*Assistant Examiner* — David C Comstock
(74) *Attorney, Agent, or Firm* — Sorell, Lenna & Schmidt, LLP

(57) ABSTRACT

A spinal implant comprises a collar, and a collet including an outer surface and an inner surface. The collet is connectable with a shaft. A crown includes a surface configured for disposal of a spinal rod. The collet is disposed with the collar such that the inner surface frictionally engages the spinal rod to capture the spinal rod with the crown. In some embodiments, implants, systems, instruments and methods are disclosed.

18 Claims, 18 Drawing Sheets

(56) References Cited

U.S. PATENT DOCUMENTS

| | | | |
|---|---|---|---|
| 11,039,864 B2 | 6/2021 | Barrus et al. | |
| 2019/0029729 A1* | 1/2019 | Mire | A61B 17/7032 |
| 2020/0246048 A1* | 8/2020 | May | A61B 17/7032 |
| 2021/0153910 A1 | 5/2021 | Kishan et al. | |
| 2021/0307791 A1 | 10/2021 | Barrus et al. | |

* cited by examiner

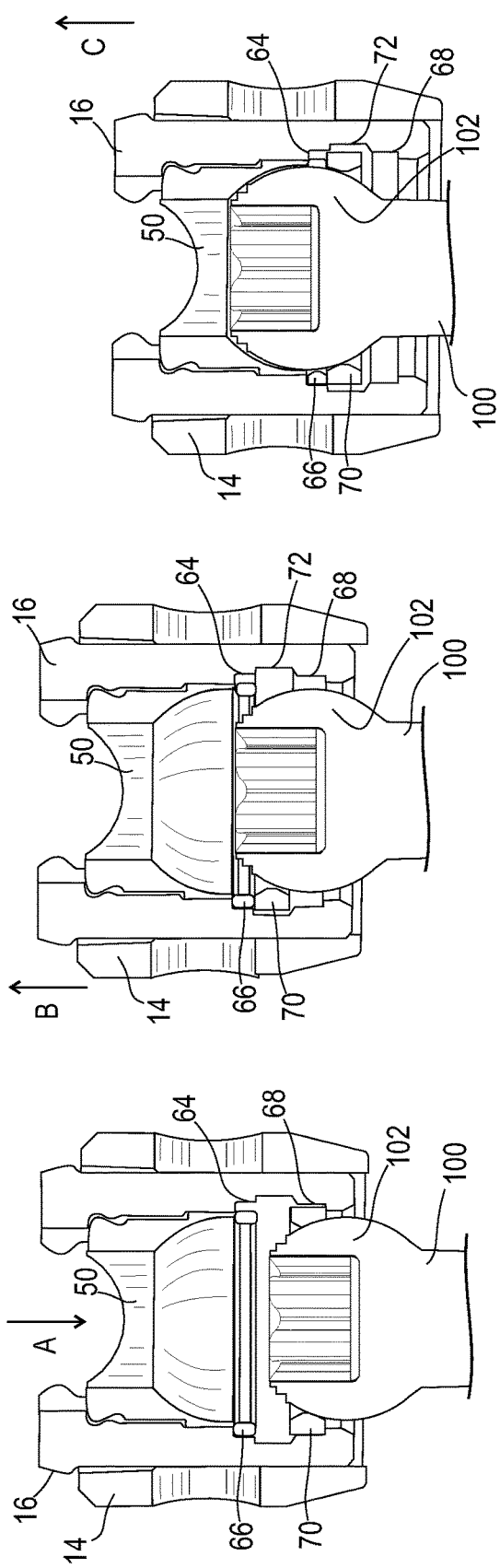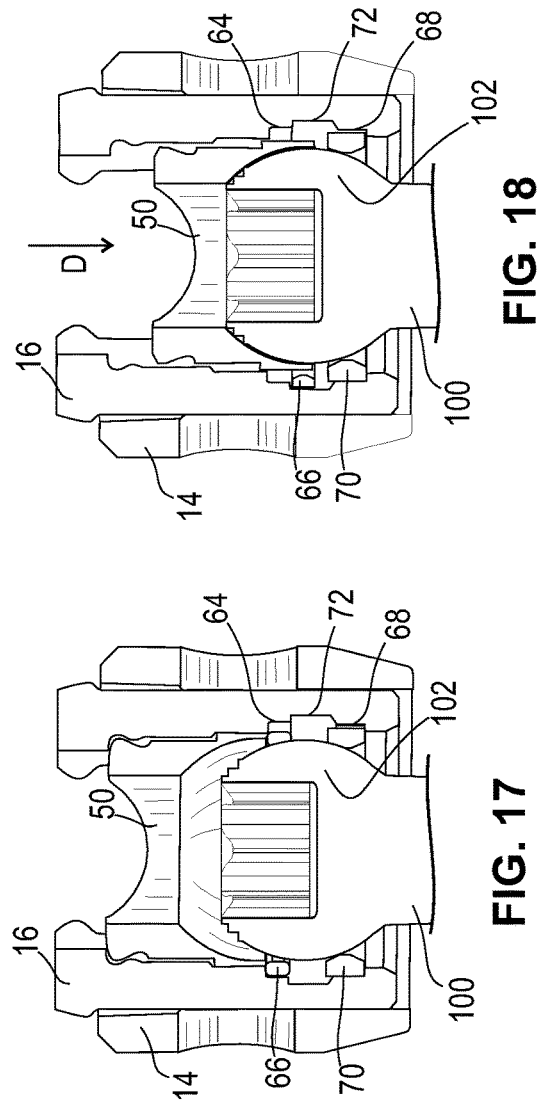

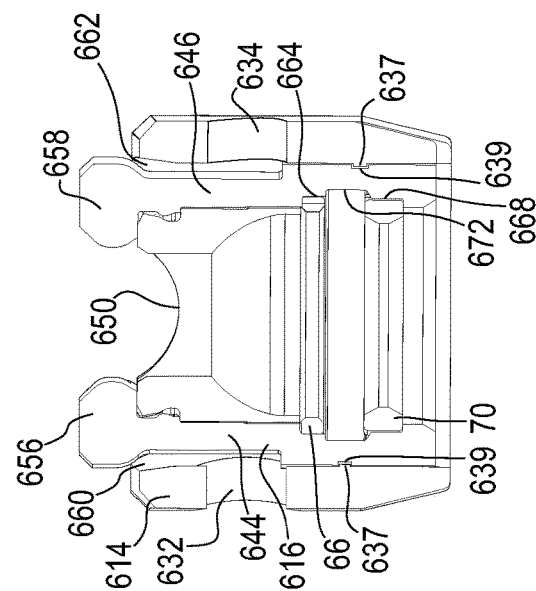

SPINAL IMPLANT SYSTEM AND METHODS OF USE

TECHNICAL FIELD

The present disclosure generally relates to medical devices for the treatment of spinal disorders, and more particularly to a surgical implant system including a bone fastener and a related method.

BACKGROUND

Spinal pathologies and disorders such as scoliosis and other curvature abnormalities, kyphosis, degenerative disc disease, disc herniation, osteoporosis, spondylolisthesis, stenosis, tumor, and fracture may result from factors including trauma, disease and degenerative conditions caused by injury and aging. Spinal disorders typically result in symptoms including deformity, pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes correction, fusion, fixation, discectomy, laminectomy and implantable prosthetics. As part of these surgical treatments, spinal constructs such as vertebral rods are often used to provide stability to a treated region. Rods redirect stresses away from a damaged or defective region while healing takes place to restore proper alignment and generally support the vertebral members. During surgical treatment, one or more rods and bone fasteners can be delivered to a surgical site. The rods may be attached via the fasteners to the exterior of two or more vertebral members. This disclosure describes an improvement over these prior technologies.

SUMMARY

In one embodiment, a spinal implant is provided. The spinal implant has a collar, and a collet including an outer surface and an inner surface. The collet is connectable with a shaft. A crown includes a surface configured for disposal of a spinal rod. The collet is disposed with the collar such that the inner surface frictionally engages the spinal rod to capture the spinal rod with the crown. In some embodiments, implants, systems, instruments and methods are disclosed.

In one embodiment, a spinal implant system is provided. The spinal implant system includes a spinal rod, and a bone fastener including a collar, and a collet having an outer surface and an inner surface. A crown is provided, and a shaft is connectable with the collet. The collet is disposed with the collar such that the inner surface frictionally engages the spinal rod to capture the spinal rod with the crown. A surgical instrument is engageable with the bone fastener.

In one embodiment, the spinal implant includes a collar, and a collet having an inner surface and being connectable with a shaft. A crown includes an inner surface and an outer surface. The collar is engageable with the collet such that the inner surface of the collet engages the outer surface of the crown such that the inner surface of the crown is frictionally engageable with a spinal rod to capture the spinal rod with the crown.

BRIEF DESCRIPTION OF THE DRAWINGS

The present disclosure will become more readily apparent from the specific description accompanied by the following drawings, in which:

FIG. 14 is a side cross section view of components of the system shown in FIG. 1;

FIG. 15 is a side cross section view of components of the system shown in FIG. 1;

FIG. 16 is a side cross section view of components of the system shown in FIG. 1;

FIG. 17 is a side cross section view of components of the system shown in FIG. 1;

FIG. 18 is a side cross section view of components of the system shown in FIG. 1;

FIG. 33 is a perspective view of components of the system shown in FIG. 32;

FIG. 34 is a perspective view of components of the system shown in FIG. 32;

FIG. 35 is a cross section view of components of the system shown in FIG. 32;

DETAILED DESCRIPTION

Figure 1:
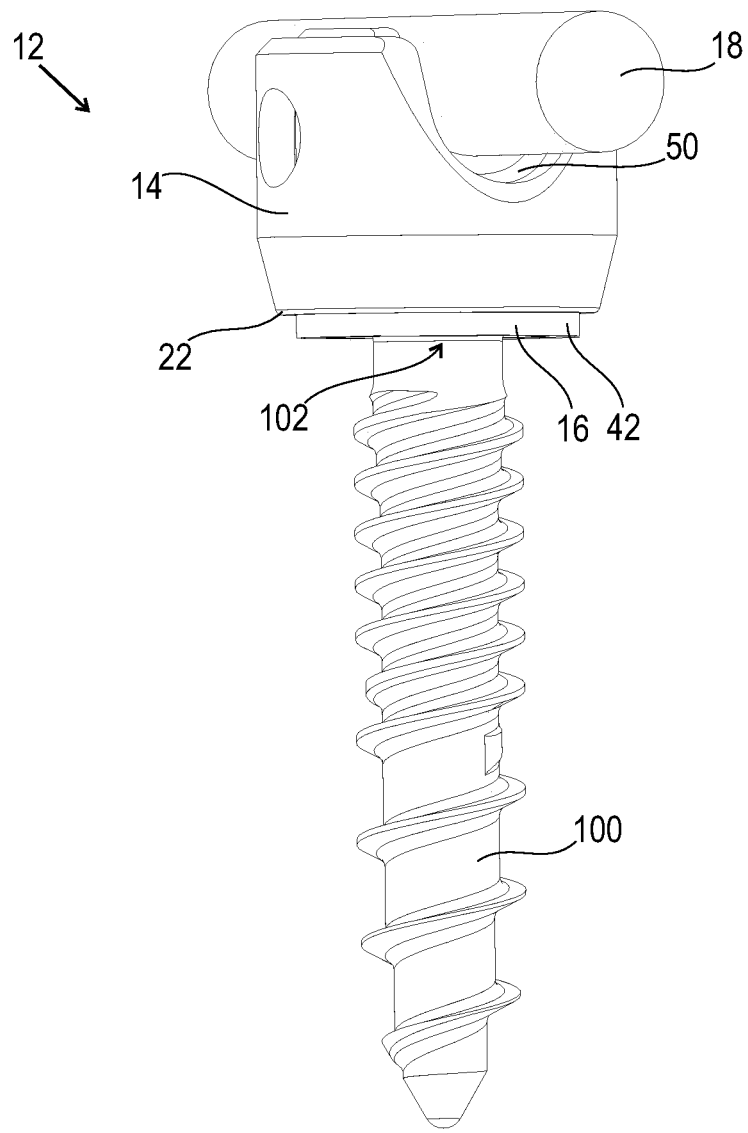
FIG. 1 is a perspective view of components of one embodiment of a spinal implant system in accordance with the principles of the present disclosure.

The exemplary embodiments of a surgical system and related methods of use disclosed are discussed in terms of medical devices for the treatment of musculoskeletal disorders and more particularly, in terms of a spinal implant system including a bone fastener. In some embodiments, the present spinal implant system includes a low profile bone fastener configured for posterior fixation. In some embodiments, the bone fastener includes a collar, and a collet disposed with the collar such that an inner surface frictionally engages a spinal rod to capture the spinal rod. In some embodiments, the systems and methods of the present disclosure are employed with a spinal joint fusion or fixation procedure, for example, with a cervical, thoracic, lumbar and/or sacral region of a spine.

In some embodiments, the present spinal implant system includes a bone fastener having a low profile that provides a reduced dorsal height orientation. In some embodiments, the bone fastener is configured for use in small stature patients and provides sufficient strength to facilitate spinal fusion. In some embodiments, the spinal implant is configured for fixation with a spinal rod. In some embodiments, the spinal implant does not include a setscrew and is configured for friction fit engagement with the spinal rod. In some embodiments, friction fit includes a compression fit engagement. In some embodiments, components of the bone fastener are configured for mating engagement with surgical instruments during a surgical procedure.

In some embodiments, the present spinal implant system includes a bone fastener including a collar, a collet, a crown and a shaft. In some embodiments, the collet is configured to fix a spinal implant, for example, a spinal rod with the bone fastener. In some embodiments, the collet is configured for disposal with the collar. In some embodiments, the crown is disposed with the collet. In some embodiments, a portion of the crown engages with the spinal rod. In some embodiments, the spinal rod is inserted into the crown and the collar is translated in an upward direction relative to the bone fastener to move surfaces of the collet inward, thereby fixing the spinal rod with the crown and the collet. In some embodiments, movement of the surfaces of the collet form a taper lock mechanism to fix the collet with the spinal rod. In some embodiments, the spinal rod is in a compression fit engagement with the collet and the crown. In some embodiments, the spinal rod is in a pressure fit engagement with the collet and the crown. In some embodiments, the bone fastener includes a low profile height and does not include a setscrew. In some embodiments, the bone fastener does not include a threaded setscrew employed in situ.

In some embodiments, the present surgical system includes a bone fastener including components that are disposed in a pre-assembled configuration prior to use. In some embodiments, the bone fastener includes a pre-assembled collet disposed within a collar. In some embodiments, the collet is fixed with the collar. In some embodiments, the collet is welded to interior surfaces of the collar. In some embodiments, the collet is staked to the collar. In some embodiments, the collet is spot welded to interior surfaces of the collar.

In some embodiments, the present surgical system includes a bone fastener including a collet. In some embodiments, the collet is disposed with a collar. In some embodiments, the collet includes a pair of arms. In some embodiments, each arm includes an inner surface. In some embodiments, the inner surfaces are configured to engage a spinal rod to capture the spinal rod with a crown. In some embodiments, the inner surfaces frictionally engage the spinal rod. In some embodiments, an inner surface of the collar and an outer surface of the collet provides clearance for the arms such that the arms can move to open and accept the spinal rod. In some embodiments, the inner surface of the collar and/or the outer surface of the collet are angled or tapered. In some embodiments, the inner surfaces engage the spinal rod in a snap fit engagement. In some embodiments, the spinal rod is in a snap fit engagement with the collet and the arms move in an outward direction. In some embodiments, the inner surfaces engage the spinal rod in a pressure fit engagement. In some embodiments, the collar is translated in an upward direction to lock or fix the spinal rod with the collet and the crown.

In some embodiments, the present spinal implant includes a shaft configured for a modular connection with the collet and/or the crown. In some embodiments, the present spinal implant provides a modular shaft that allows selection of alternately configured collets and/or crowns. In some embodiments, the various collets and/or crowns are provided in a kit. In some embodiments, an interior surface of the collet defines a plurality of grooves. In some embodiments, the plurality of grooves include an upper groove, an expansion groove and a lower groove. In some embodiments, the spinal implant includes a plurality of rings. In some embodiments, the plurality of rings include an upper ring and a lower ring. In some embodiments, the plurality of rings are configured for disposal within the plurality of grooves such that a head of the shaft is fixed with the collet. In some embodiments, the modular connection can be assembled in situ.

In some embodiments, the present surgical system includes a bone fastener including a collar and a collet. In some embodiments, the collet is configured for disposal within the collar. In some embodiments, the collet is fixed relative to the collar to prevent disassembly. In some embodiments, the collet and the collar are fixed via an outer surface including a mating surface of the collet that engages with an inner surface including a mating surface of the collar. In some embodiments, the mating surfaces include a male/female engagement. In some embodiments, the mating surface of the collar includes a projection and the mating surface of the collet includes a groove. In some embodiments, the mating surfaces include a shear and/or break away feature. In some embodiments, the inner surface of the collar is deformable such that the mating surface engages with the mating surface of the collet to prevent rotation of the collar when in a non-keyed position.

In some embodiments, the present surgical system includes a bone fastener including a collar, a collet, a crown, and a shaft. In some embodiments, the crown is configured for disposal within the collet. In some embodiments, the crown and the collet are configured for engagement with a spinal rod. In some embodiments, the crown includes a pair of arms. In some embodiments, in an assembled configuration, the arms of the crown extend beyond a proximal end of the collet. In some embodiments, the collet includes a pair of arms. In some embodiments, the arms of the collet move in an inward direction, to push the arms of the crown into engagement with the spinal rod. In some embodiments, the arms of the crown increase a surface area of the crown that engages the spinal rod. In some embodiments, the arms of the crown increase axial grip performance of the crown with the spinal rod.

In some embodiments, the present surgical system is employed with a method of assembling the bone fastener including the step of disposing a pre-assembled collar including a collet, a crown, an upper ring and a lower ring onto a head of a screw shaft. In some embodiments, the upper ring translates in a downward direction relative to a head of the shaft with the crown and snaps open. In some embodiments, the upper ring is installed in a compressed state within an upper groove of the collet. In some embodiments, the upper ring fixes the head of the shaft to the collet since the lower ring can no longer enter an expansion groove of the collet. In some embodiments, the method includes the step of driving the crown to lock the head with the crown. In some embodiments, the method of assembly is performed in situ.

In some embodiments, the present surgical system is employed with a method of pre-assembling the bone fastener including the step of splaying a collet open with an assembly tool such that the collet is configured to accept a selected dimension of a spinal rod. In some embodiments, the method includes the step of sliding a collar onto the collet. In some embodiments, the method of sliding the collar onto the collet facilitates outer surfaces of arms of the collet to contact an inner surface of the collar at an end of the collar. In some embodiments, the method includes the step of welding the collet with the collar. In some embodiments, the step of welding includes spot welding. In some embodiments, the step of welding includes seam welding. In some embodiments, the collet and the collar are welded such that disengagement between the collar and the collet requires a force to be applied to the collar and the collet of 2000 to 3000 Newtons (N). In some embodiments, the method includes the step of removing the assembly tool from the collet. In some embodiments, the method includes the step of snapping a crown into the collet. In some embodiments, the method includes the step of assembling an upper ring and a lower ring with the collet. In some embodiments, the method includes the step of fixing a head of a shaft with the collet, as described herein.

In some embodiments, the present surgical system is employed with a method of assembling the bone fastener including the step of engaging a surgical instrument, including a surgical inserter with a pre-assembled collar. In some embodiments, the pre-assembled collar further includes a collet, a crown, an upper ring and a lower ring. In some embodiments, the method includes the step of actuating the surgical instrument until a trigger of the surgical instrument locks onto the collet. In some embodiments, actuating the surgical instrument includes manually squeezing a pair of handles of the surgical instrument. In some embodiments, spring loaded distal tips of the surgical instrument are configured to splay in a lateral orientation as the pair of handles are squeezed to lock onto the collet. In some embodiments, the method includes the step of attaching the pre-assembled collar onto a head of a shaft. In some embodiments, the method comprises the step of translating the surgical instrument in an upward direction to confirm connection of the pre-assembled collar with the shaft. In some embodiments, the method comprises the step of actuating the trigger. In some embodiments, the method comprises the step of actuating the pair of handles to drive the crown in a direction relative to the shaft.

In some embodiments, the present surgical system is employed with a method of reducing a spinal rod with the spinal implant including the step of engaging a surgical instrument, including a sliding lock rod reducer with a collar of the bone fastener. In some embodiments, the sliding lock rod reducer facilitates sagittal pivoting of the sliding lock rod reducer relative to the collar. In some embodiments, the sliding lock rod reducer includes a pair of arms. In some embodiments, each arm pivots in a lateral direction to connect and disconnect from the collar. In some embodiments, the sliding lock rod reducer includes an actuator, including a quick advance button. In some embodiments, each arm includes an inner surface that defines a ramp. In some embodiments, each ramp includes a rod centering ramp. In some embodiments, a force required to seat the spinal rod with the bone fastener is less than a weld strength of the collar and collet. In some embodiments, a force applied to the spinal rod includes about 6 to 7 Newton-meters (Nm) to generate an axial force to fracture a weld between the collar and the collet to tighten a spinal rod onto the bone fastener.

In some embodiments, the present surgical system is employed with a method of disengaging the spinal rod from the bone fastener including the step of engaging a surgical instrument, including a sliding lock revision instrument with the spinal rod. In some embodiments, the engaging step includes disposing an end of the sliding lock revision instrument about a portion of the spinal rod and rotating tabs of the sliding lock revision instrument under the spinal rod. In some embodiments, the sliding lock revision instrument includes an outer sleeve and an inner threaded plunger. In some embodiments, the method includes the step of threading the inner threaded plunger in a downward direction relative to the spinal rod to push a slider of the sliding lock revision instrument in a downward direction relative to the spinal rod to disengage the spinal rod from the bone fastener. In some embodiments, a distal portion of the inner threaded plunger rotates relative to a top driver portion such that a tip contours around the spinal rod while driving the slider.

In some embodiments, a bone fastener is configured for assembly without the use of an instrument, for example, a practitioner, surgeon and/or medical staff utilizes manual assembly. In some embodiments, the system requires minimal force to attach an implant receiver and a screw shaft assembly in-situ thereby reducing a pre-load on the vertebrae, for example, the pedicle.

In some embodiments, the present disclosure may be employed to treat spinal disorders for example, degenerative disc disease, disc herniation, osteoporosis, spondylolisthesis, stenosis, scoliosis and other curvature abnormalities, kyphosis, tumor and fractures. In some embodiments, the present disclosure may be employed with other osteal and bone related applications, including those associated with diagnostics and therapeutics. In some embodiments, the disclosed spinal implant system may be alternatively employed in a surgical treatment with a patient in a prone or supine position, and/or employ various surgical approaches to the spine, including anterior, posterior, posterior mid-line, lateral, postero-lateral, and/or antero-lateral approaches, and in other body regions. The present disclosure may also be alternatively employed with procedures for treating the lumbar, cervical, thoracic, sacral and pelvic regions of a spinal column. The spinal implant system of the present disclosure may also be used on animals, bone models and other non-living substrates, for example, in training, testing and demonstration.

The present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. In some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

As used in the specification and including the appended claims, "treating" or "treatment" of a disease or condition refers to performing a procedure that may include administering one or more drugs to a patient (human, normal or otherwise or other mammal), employing implantable devices, and/or employing instruments that treat the disease, for example, microdiscectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, ligaments, tendons, cartilage and/or bone unless specifically referred to otherwise.

The following discussion includes a description of a surgical system including a bone fastener, related components and methods of employing the surgical system in accordance with the principles of the present disclosure. Alternate embodiments are also disclosed. Reference is made in detail to the exemplary embodiments of the present disclosure, which are illustrated in the accompanying figures. Turning to FIGS. 1-31, there are illustrated components of a spinal implant system 10.

The components of spinal implant system 10 can be fabricated from biologically acceptable materials suitable for medical applications, including metals, synthetic polymers, ceramics and bone material and/or their composites. For example, the components of spinal implant system 10, individually or collectively, can be fabricated from materials such as stainless steel alloys, commercially pure titanium, titanium alloys, Grade 5 titanium, super-elastic titanium alloys, cobalt-chrome alloys, superelastic metallic alloys (e.g., Nitinol, super elasto-plastic metals, such as GUM METAL®), ceramics and composites thereof such as calcium phosphate (e.g., SKELITE™), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, for example, composites of metals and calcium-based ceramics, composites of PEEK and calcium based ceramics, composites of PEEK with resorbable polymers, totally resorbable materials, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplaetohe and their combinations.

Various components of spinal implant system 10 may have material composites, including the above materials, to achieve various desired characteristics such as strength, rigidity, elasticity, compliance, biomechanical performance, durability and radiolucency or imaging preference. The components of spinal implant system 10, individually or collectively, may also be fabricated from a heterogeneous material such as a combination of two or more of the above-described materials. The components of spinal implant system 10 may be monolithically formed, integrally connected or include fastening elements and/or instruments, as described herein.

Figure 2:
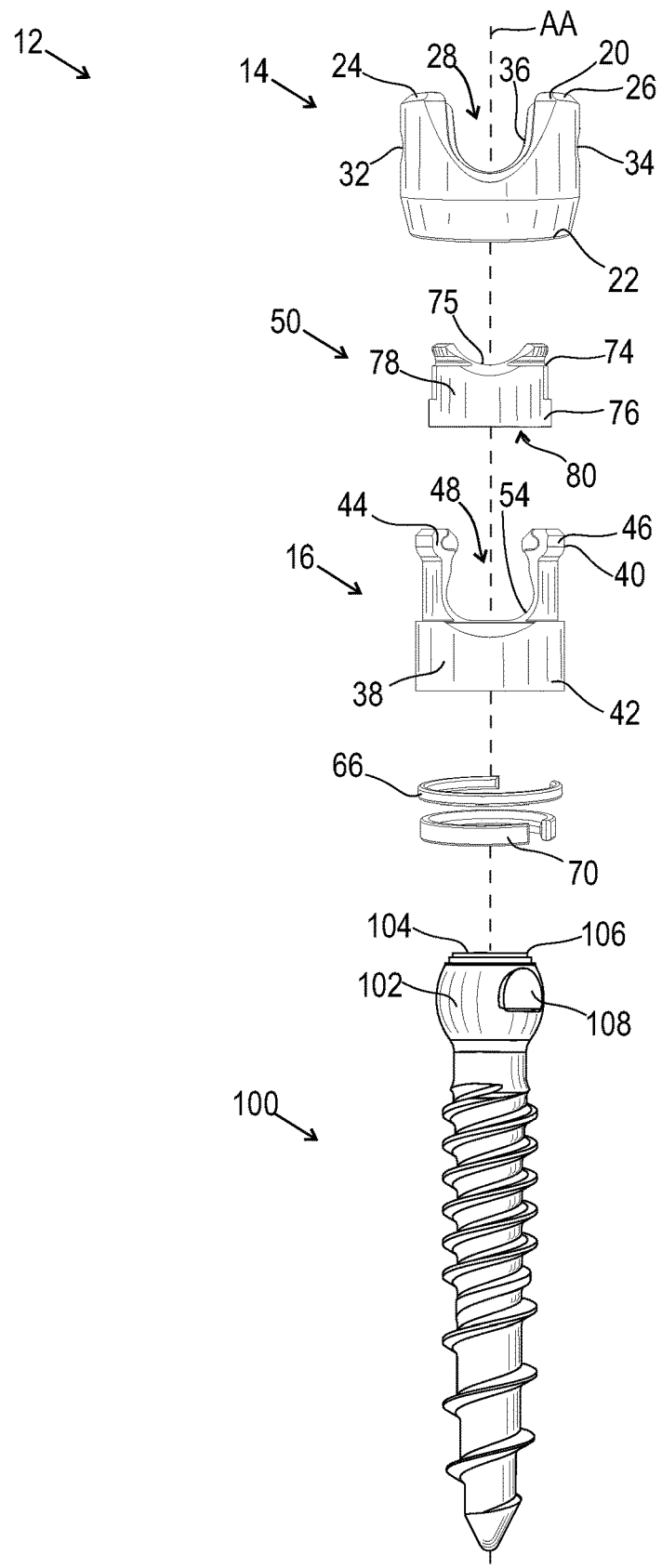
FIG. 2 is a perspective view of components of the system shown in FIG. 1 with parts separated.
Figure 4:
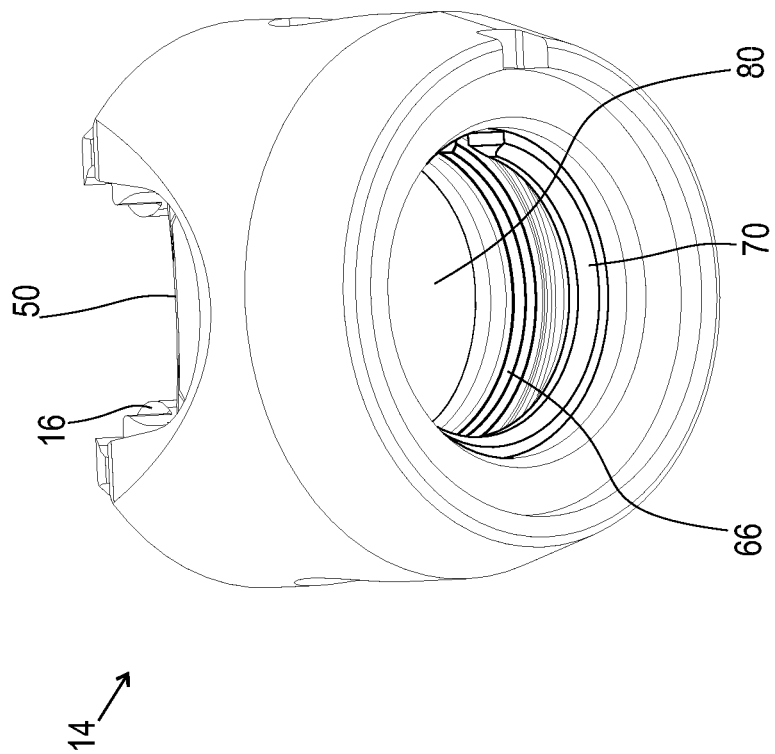
FIG. 4 is a perspective view of components of the system shown in FIG. 1.
Figure 3:
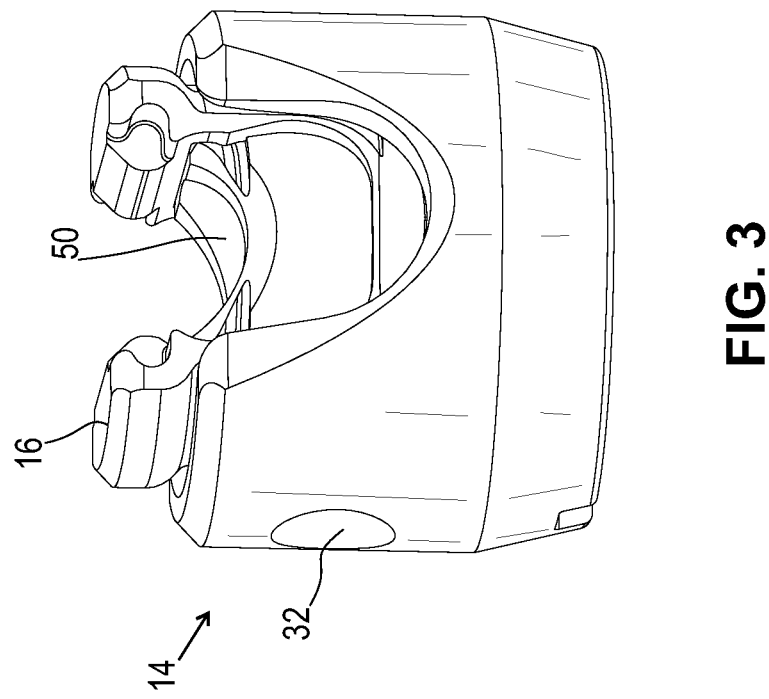
FIG. 3 is a perspective view of components of the system shown in FIG. 1.

Spinal implant system 10 includes a spinal implant, for example, a bone fastener 12. Bone fastener 12 includes a collar 14, as shown in FIGS. 1 and 2. Collar 14 is configured for engagement with a collet 16 to capture a spinal rod 18 via frictional engagement, as described herein. In some embodiments, collar 14 includes a tulip shaped receiver configuration. Collar 14 includes an end 20, an end 22, and defines a longitudinal axis AA. Collar 14 includes a pair of spaced apart arms 24, 26 that define a cavity 28 therebetween configured for disposal of collet 16.

In some embodiments, arms 24, 26 each extend parallel to axis AA. Arms 24, 26 each include an arcuate outer surface extending between a pair of side surfaces. At least one of the outer surfaces and the side surfaces of arms 24, 26 may have at least one recess or cavity 32, 34 therein, configured to receive an insertion tool, compression instrument and/or instruments for inserting and tensioning bone fastener 12.

Collar 14 includes an inner surface 36 engageable with an outer surface 38 of collet 16. In some embodiments, inner surface 36 can include a surface that is rough, arcuate, undulating, mesh, porous, semi-porous, dimpled and/or textured to enhance engagement with collet 16. In some embodiments, inner surface 36 includes a tapered configuration. End 22 is configured for engagement with a head 102 of a shaft 100.

Collet 16 extends between an end 40 and an end 42. End 42 is configured for connection with head 102 of shaft 100. In some embodiments, collet 16 is manually engageable with shaft 100 to connect collet 16 and shaft 100 in a non-instrumented snap-fit assembly, as described herein.

Collet 16 includes a pair of spaced apart arms 44, 46 at end 40 that define a cavity 48 therebetween configured for disposal of a crown 50. In some embodiments, arms 44, 46 each extend parallel to axis AA. In some embodiments, arms 44, 46 are angled relative to axis AA when bone fastener 12 is in an unassembled configuration. Collar 14 is engageable with outer surface 38 of collet 16 such that arms 44, 46 are movable inwardly to frictionally engage spinal rod 18, as described herein.

Figure 7:
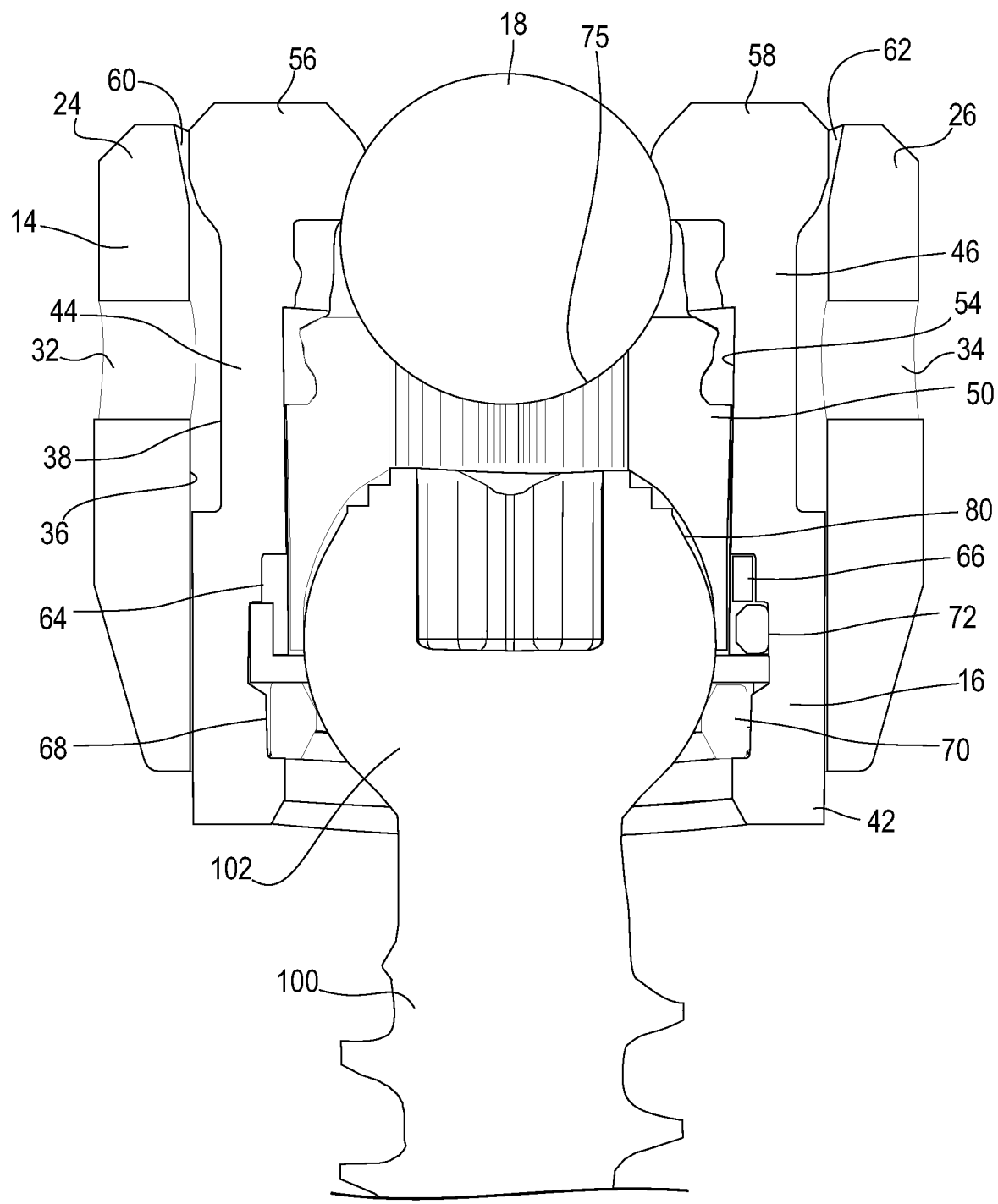
FIG. 7 is a side cross section view of the components shown in FIG. 1.

Collet 16 includes outer surface 38 and an inner surface 54, and a portion of each surface 38, 54 forms arms 44, 46. Outer surface 38 of arm 44 includes a projection, for example, a radial flange 56 and outer surface 38 of arm 46 defines a projection, for example, a radial flange 58. Radial flanges 56, 58 are configured for engagement with tapered inner surfaces 60, 62 of collar 14, such that inner surface 54 of collet 16 frictionally engages spinal rod 18 to capture spinal rod 18 with crown 50, as shown in FIG. 7. In some embodiments, movement of inner surface 54 of collet 16 forms a taper lock mechanism to fix collet 16 and crown 50 with spinal rod 18.

In some embodiments, spinal rod 18 is disposed in a compression fit engagement with collet 16 and crown 50. In some embodiments, spinal rod 18 is disposed in a pressure fit engagement with collet 16 and crown 50.

Figure 10:
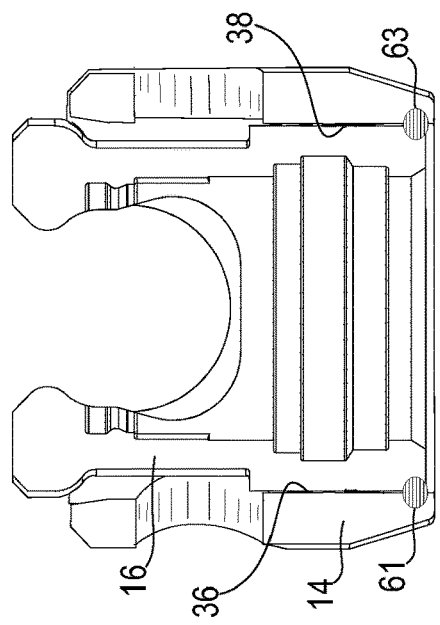
FIG. 10 is a cross section view of the components shown in FIG. 10.

In some embodiments, outer surface 38 of collet 16 is fixed with inner surface 36 of collar 14, as shown in FIG. 10. For example, outer surface 38 of collet 16 is welded to inner surface 36 of collar 14 at weld points 61, 63. In some embodiments, collet 16 is spot welded or laser welded to collar 14. In some embodiments, collet 16 is affixed to collar 14 through a mechanical stake, a shear pin, or through the use of an adhesive, such as epoxy resin. In some embodiments, collet 16 and collar 14 are welded such that disengagement between collar 14 and collet 16 require a force to be applied to collar 14 and collet 16 of 2000 to 3000 N. In some embodiments, collet 16 is disposed with collar 14 in a pre-assembled configuration prior to use. In some embodiments, collar 14 is connected to collet 16 via one or more shear tabs. In some embodiments, collar 14 includes one or more shear tabs that are configured to engage with one or more grooves, channels, or openings of collet 16 and are configured to shear off when a load is applied. In some embodiments, collet 16 includes one or more shear tabs and collar 14 includes one or more grooves, channels or openings.

Figure 6:
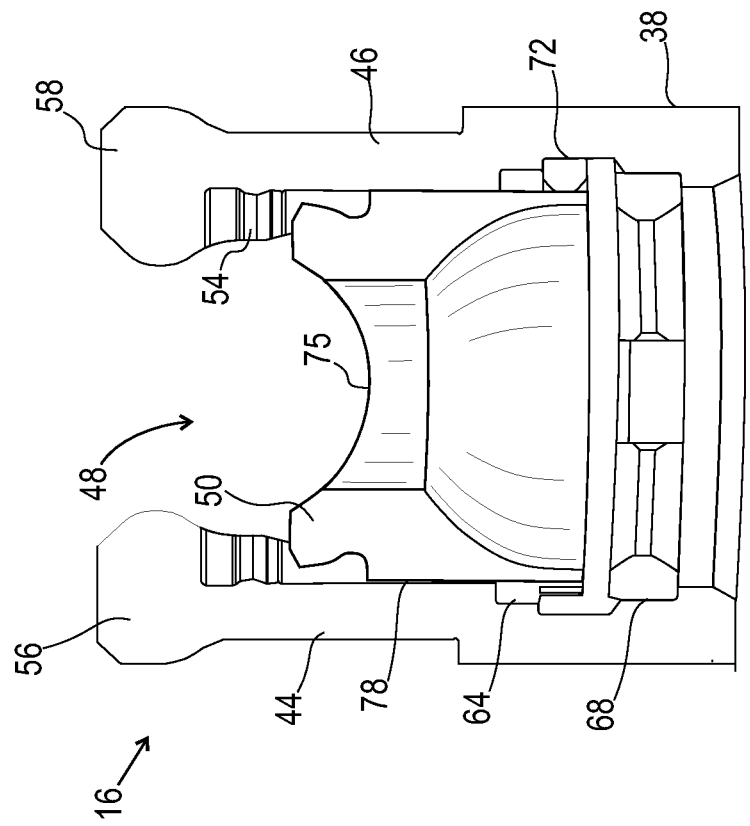
FIG. 6 is a cross section view of the components shown in FIG. 5.
Figure 5:
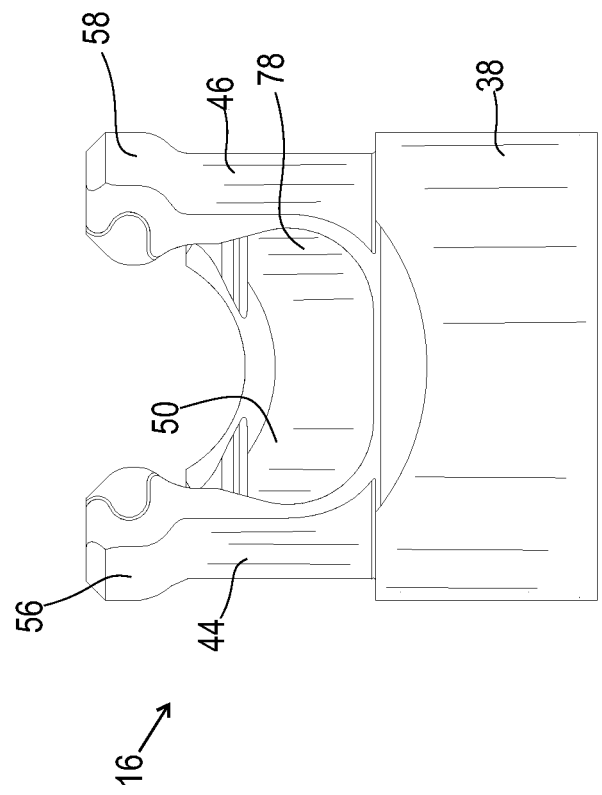
FIG. 5 is a perspective view of components of the system shown in FIG. 1.

Inner surface 54 defines a circumferential upper groove 64, as shown in FIGS. 6 and 7. Upper groove 64 is configured for disposal of a resilient member, for example, a ring 66. Ring 66 is contractable in upper groove 64. Ring 66 includes a circumference that defines an opening, for example, a gap. In some embodiments, the gap is sized such that the gap has a thickness that is less than the height and the width. In some embodiments, the gap is sized to allow ring 66 to translate through cavity 48 by contracting circumferentially. In some embodiments, upon disposal of ring 66 with upper groove 64, surfaces of upper groove 64 resist and/or prevent axial translation of ring 66 relative to longitudinal axis AA.

Inner surface 54 defines a circumferential lower groove 68. Lower groove 68 is configured for disposal of a resilient member, for example, a ring 70. Ring is expandable in lower groove 68 to connect collet 16 and shaft 100. Ring 70 includes a circumference that defines an opening, for example, a gap. In some embodiments, the gap is sized such that the gap has a thickness that is less than the height and the width. In some embodiments, the gap is sized to allow ring 70 to translate through cavity 48 by contracting circumferentially. In some embodiments, upon disposal of ring 70 with lower groove 68, surfaces of lower groove 68 resist and/or prevent axial translation of ring 70 relative to longitudinal axis AA. Inner surface 54 defines an expansion groove 72.

Rings 66, 70 facilitate manual engagement/connection of collet 16 and shaft 100. In some embodiments, rings 66, 70 facilitate manual engagement/connection of collet 16 and shaft 100 such that shaft 100 is attached with receiver 14 in a non-instrumented snap-fit assembly, as described herein.

In some embodiments, manual engagement and/or non-instrumented assembly includes a practitioner, surgeon and/or medical staff grasping shaft 100 and collet 16 and forcibly snap fitting the components together, as described herein. In some embodiments, manual engagement and/or non-instrumented assembly includes a practitioner, surgeon and/or medical staff grasping shaft 100 and collet 16 and forcibly pop fitting the components together and/or pop fitting collet 16 onto shaft 100, as described herein. In some embodiments, a force in a range of 2-50 N is required to manually engage shaft 100 and collet 16 and forcibly assemble the components. For example, a force in a range of 2-50 N is required to snap fit and/or pop fit assemble shaft 100 and collet 16. In some embodiments, a force in a range of N is required to manually engage shaft 100 and collet 16 and forcibly assemble the components. For example, a force in a range of 5-10 N is required to snap fit and/or pop fit assemble shaft 100 and collet 16. In some embodiments, shaft 100 is manually engaged with collet 16 in a non-instrumented assembly, as described herein, such that removal of collet 16 and shaft 100 requires a force and/or a pull-out strength of at least 5000 N. In some embodiments, this configuration provides manually engageable components that are assembled without instrumentation, and subsequent to assembly, the assembled components have a selected pull-out strength and/or can be pulled apart, removed and/or separated with a minimum required force.

Crown 50 includes an end 74 and an end 76, as shown in FIG. 2. Crown 50 is configured for disposal with collet 16 and is configured to capture spinal rod 18. End 74 includes a surface that defines an implant receiving surface 75 configured for disposal with spinal rod 18. Crown 50 includes an outer surface 78 configured for engagement with collet 16, and an inner surface 80 configured for engagement with head 102 of shaft 100.

Collar 14 is translatable relative to collet 16 between a first, non-locking orientation and a second, locking orientation such that implant receiving surface of crown 50 frictionally engages spinal rod 18 to capture spinal rod 18 with crown 50. In the non-locking orientation, radial flanges 56, 58 of collet 16 do not engage with tapered inner surfaces 60, 62 of collar 14. In the locking orientation, collar 14 is translatable relative to collet 16 such that tapered inner surfaces 60, 62 of collar 14 engage with radial flanges 56, 58 of collet 16, and inner surface 54 of collet 16 frictionally engages spinal rod 18 to capture spinal rod 18 with crown 50.

Bone fastener 12 includes shaft 100 and head 102. Shaft 100 is configured to penetrate tissue, for example, vertebral tissue. In some embodiments, shaft 100 includes an outer surface having an external thread form. In some embodiments, the external thread form may include a single thread turn or a plurality of discrete threads. Head 102 includes a tool engaging portion 104 configured to engage a surgical tool or instrument, as described herein. In some embodiments, portion 104 includes a hexagonal cross-section. Head 102 includes a surface that defines a plurality of ridges 106 to improve purchase of head 102 with crown 50. In some embodiments, head 102 includes an outer surface having planar surfaces or flats 108 and/or arcuate surfaces.

In some embodiments, collet 16 may be disposed with head 102 in alternate fixation configurations, for example, friction fit, pressure fit, locking protrusion/recess, locking keyway and/or adhesive. In some embodiments, collet 16 is configured for rotation relative to head 102 for multi-axial movement. In some embodiments, collet 16 is configured for rotation in range of 360 degrees relative to head 102 to facilitate positioning of shaft 100 with tissue. In some embodiments, collet 16 is configured for selective rotation in range of 360 degrees relative to and about head 102 such that shaft 100 is selectively aligned for rotation in a plane relative to collet 16. In some embodiments, collet 16 may be disposed with head 102 in a uni-axial configuration or a sagittally adjustable configuration.

In some embodiments, spinal implant system 10 includes a spinal implant kit, as described herein, which includes a plurality of screw shaft assemblies 100 and/or collar 14/collet 16 assemblies. Screw shaft assembly 100 and/or collar 14/collet 16 assembly is configured for selection such that the components of bone fastener 12 are interchangeable.

In assembly, operation and use, spinal implant system 10, similar to the systems and methods described herein, is employed with a surgical procedure for treatment of a spinal disorder affecting a section of a spine of a patient, as discussed herein. Spinal implant system 10 is employed with a surgical procedure for treatment of a condition or injury of an affected section of the spine.

Figure 9:
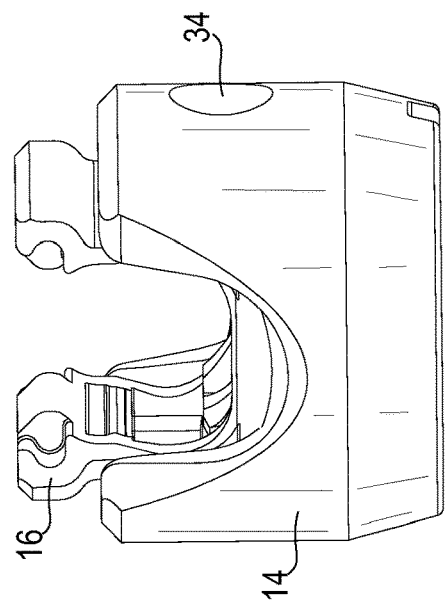
FIG. 9 is a perspective view of components of the system shown in FIG. 1.
Figure 8:
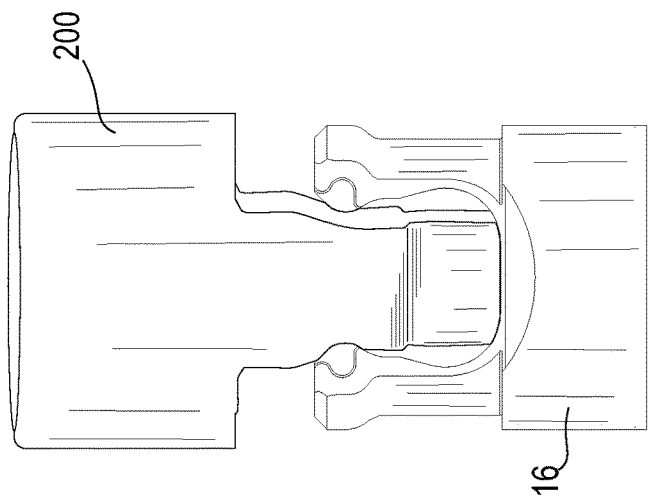
FIG. 8 is a perspective view of components of the system shown in FIG. 1 disposed with a surgical tool.

In some embodiments, selected components of bone fastener 12 are disposed in a pre-assembled configuration prior to use in a surgical procedure. To pre-assemble selected components of bone fastener 12, as shown in FIGS. 8-10, collet 16 is splayed open with an assembly tool 200, as shown in FIG. 8. In some embodiments, collet 16 is splayed open to accept a selected spinal rod 18. Collar 14 slidingly engages onto collet 16, as shown in FIG. 9. In some embodiments, sliding collar 14 onto collet 16 facilitates outer surfaces of arms 44, 46 of collet 16 to contact inner surface 36 of collar 14 at end 20 of collar 14. Collet 16 is welded with collar 14 at weld points 61, 63, as shown in FIG. 10. In some embodiments, collet 16 and collar 14 are welded such that disengagement between collar 14 and collet 16 requires an application of force to be applied to collar 14 and collet 16 of 2000 to 3000 N. Assembly tool 200 is removed from collet 16. Crown 50 is disposed with collet 16. In some embodiments, crown 50 is snapped into collet 16. Upper ring 66 and lower ring 70 are disposed with collet 16.

In some embodiments, shaft 100 is selected from a kit of a plurality of shafts 100 for interchangeable connection with preassembled components of bone fastener 12, described herein to comprise bone fastener 12 having a selected movement, similar to those described herein. In some embodiments, the kit includes a variety of shafts 100 having different movement configurations when assembled with preassembled components of bone fastener 12, for example, multi-axial movement, sagittal angulation movement, fixed axis movement, mono-axial movement and/or uni-planar movement.

Figure 13:
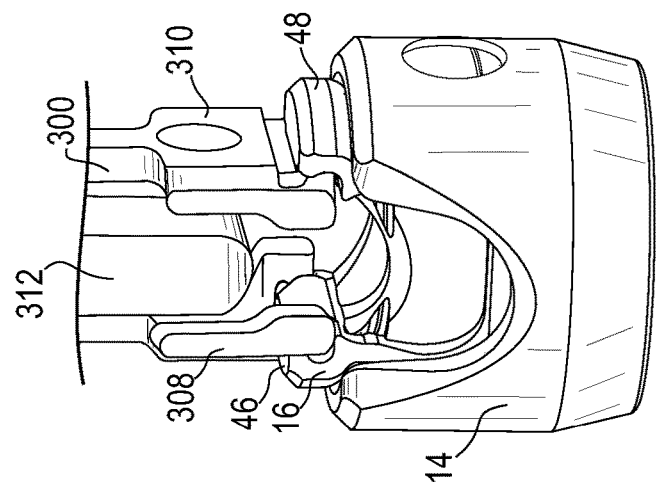
FIG. 13 is an enlarged breakaway view of components of the system shown in FIG. 11.
Figure 12:
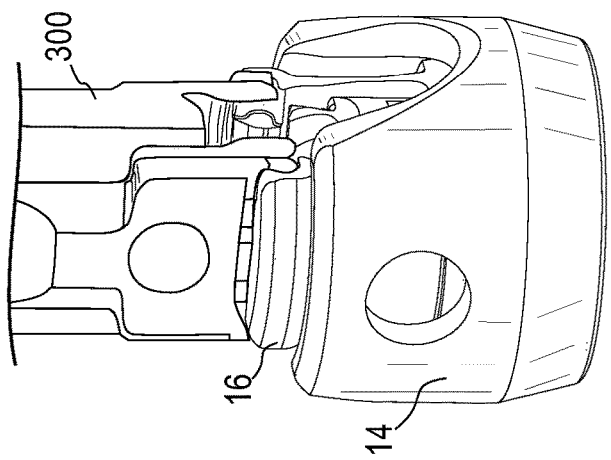
FIG. 12 is an enlarged breakaway view of components of the system shown in FIG. 11.
Figure 11:
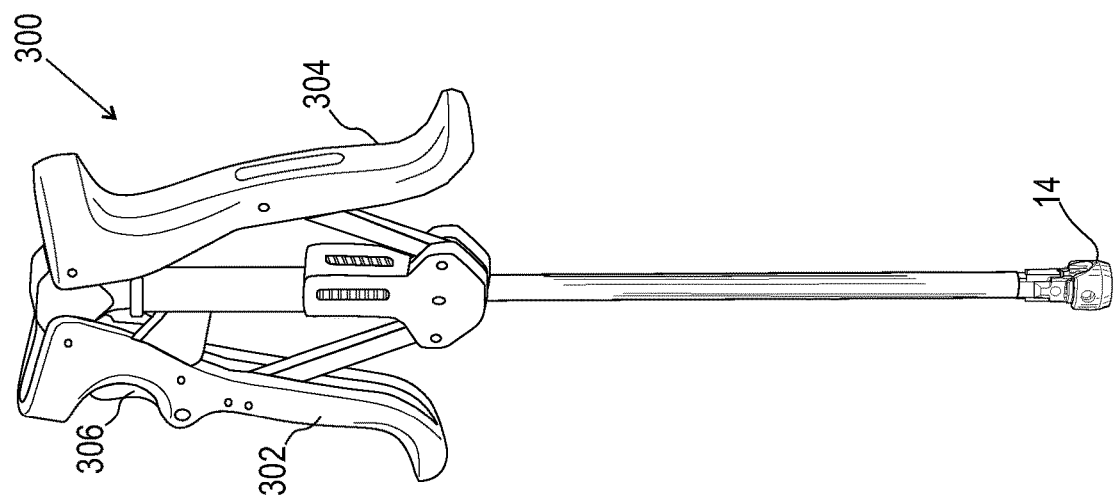
FIG. 11 is a perspective view of components of one embodiment of a spinal implant system in accordance with the principles of the present disclosure.
Figure 21:
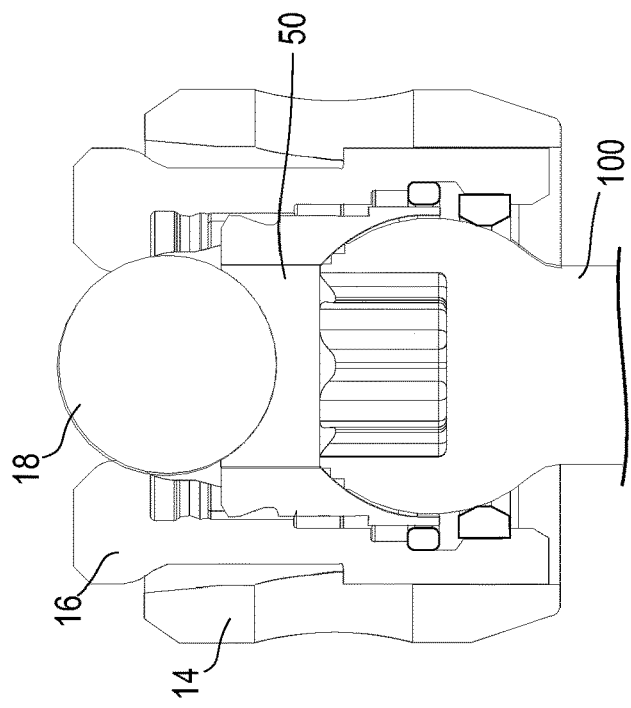
FIG. 21 is a side cross section view of components of the system shown in FIG. 1.

Ring 66 is disposed with upper groove 64 and ring 70 is disposed with lower groove 68 in a contracted orientation. In some embodiments, bone fastener 12 is disposed adjacent vertebrae at a surgical site and is manipulated to drive, torque, insert or otherwise connect shaft 100 with vertebrae in connection with a surgical procedure, as described herein. A surgical instrument, for example, a surgical inserter 300, as shown in FIGS. 11-13, is implemented to engage with collet 16 and to fix collet 16 with head 102 of shaft 100. See also, for example, the embodiments and disclosure of an inserter and method for surgically treating a spine, shown and described in commonly owned and assigned U.S. patent application Ser. No. 17/846,419 filed Jun. 22, 2022, and published as U.S. Patent Application Publication No. 2022/0387084, on Dec. 8, 2022, the entire contents of which being incorporated herein by reference.

An actuator, for example, handles 302, 304 are actuated until a trigger, for example, a button 306 locks. In some embodiments, handles 302, 304 are actuated by a user manually squeezing handles 302, 304. Spring loaded distal tips 308, 310, splay in an orientation, for example, a lateral orientation while handles 302, 304 are squeezed to lock distal tips 308, 310 onto collet 16.

Shaft 100 is engageable, as described herein, with collet 16, as shown in FIG. 14. Collet 16 is assembled with shaft 100 by translating collet 16 in a direction shown by arrow A in FIG. 14 via inserter 300. Inserter 300 is translated in a direction shown by arrow B in FIG. 15 to confirm connection of collet 16 and collar 14 with shaft 100. Engagement of head 102 with collet 16 causes a surface of head 102 to engage with ring 70 such that ring 70 is translated, in the direction shown by arrow B, disposing ring 70 into expansion groove 72 in an expanded orientation. Head 102 translates further through collet 16 in the direction shown by arrow C in FIG. 16 and passes further through ring 70 as ring 70 is driven back into groove 68, shown in FIGS. 16 and 17. Ring 70 resiliently contracts into its natural state around head 102 as flats 108 engage with inner surface 80 of crown 50 to provisionally capture shaft 100.

Button 306 and handles 302, 304 of inserter 300 are actuated to translate an inner shaft 312 in a direction shown by arrow D in FIG. 18 to engage crown Outer surface 78 of crown 50 engages ring 66 to dispose ring 66 into groove 72 such that ring 66 resiliently opens into an expanded orientation. Ring 66 is oriented for abutting and/or contacting engagement with ring 70 to resist and/or prevent translation of ring 70 from groove 68 into groove 72, and thus providing fixed connection of the components of bone fastener 12 including permanent capture of head 102 and shaft 100. Inserter 300 is then disconnected from bone fastener 12.

As shown in FIGS. 19-23, to capture spinal rod 18 with bone fastener 12, a surgical instrument, for example, a rod reducer 400, shown in FIGS. 24-28 is employed for connection with collar 14. In some embodiments, rod reducer 400 facilitates sagittal pivoting of rod reducer 400 relative to collar 14. See also, for example, the embodiments and disclosure of a rod reducer and method for surgically treating a spine, shown and described in commonly owned and assigned U.S. Pat. No. 11,202,661, the entire contents of which being incorporated herein by reference.

Figure 20:
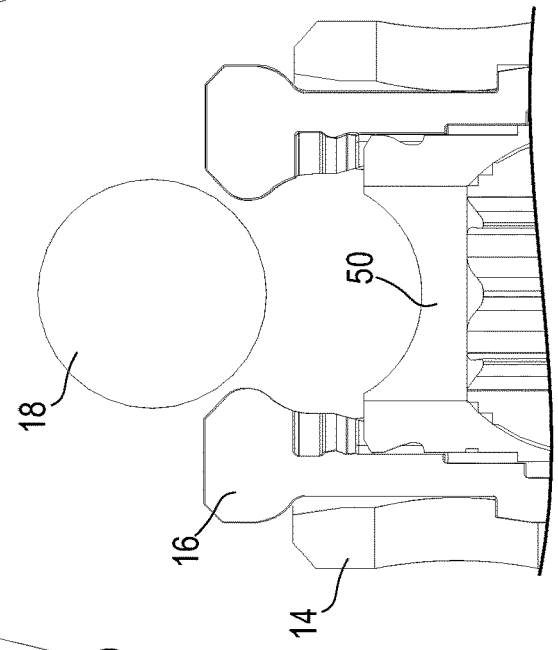
FIG. 20 is a side cross section view of components of the system shown in FIG. 1.
Figure 19:
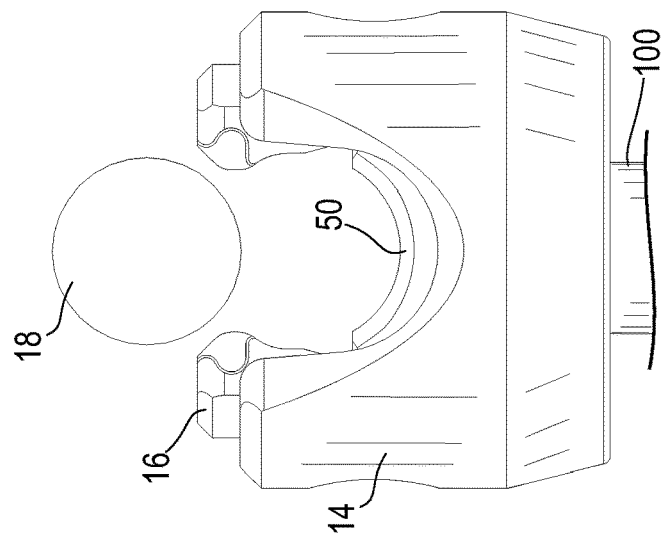
FIG. 19 is a side view of components of the system shown in FIG. 1.
Figure 23:
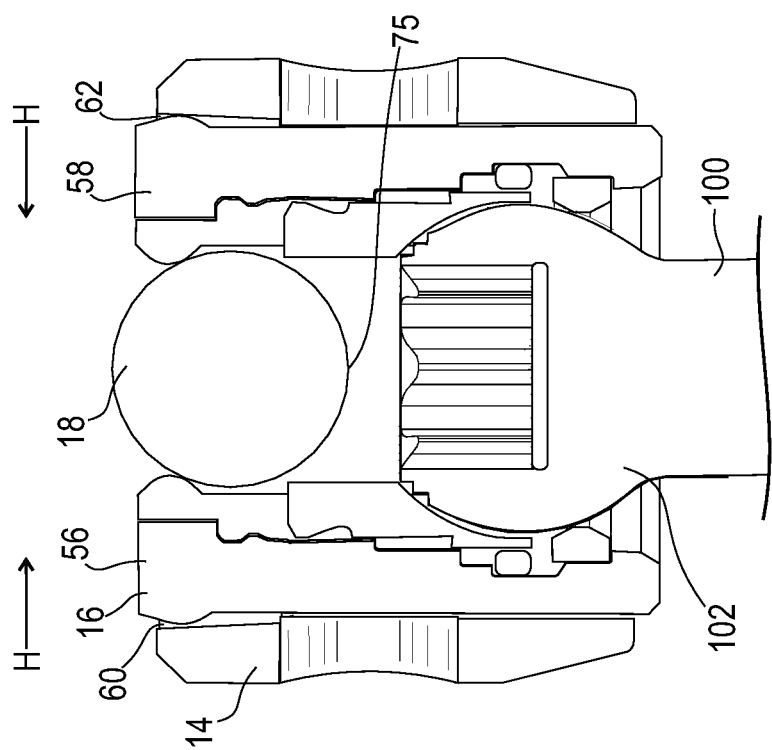
FIG. 23 is a side cross section view of components of the system shown in FIG. 1.
Figure 22:
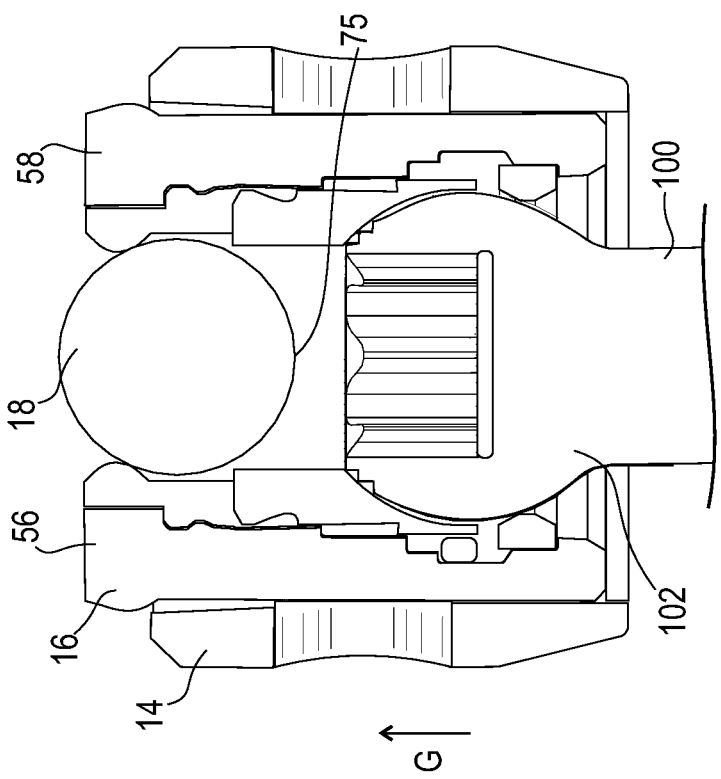
FIG. 22 is a side cross section view of components of the system shown in FIG. 1.
Figure 26:
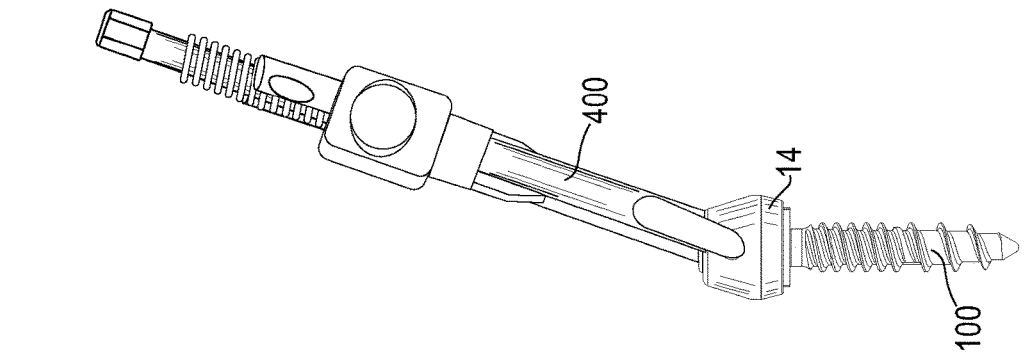
FIG. 26 is a perspective view of the components shown in FIG. 24.
Figure 25:
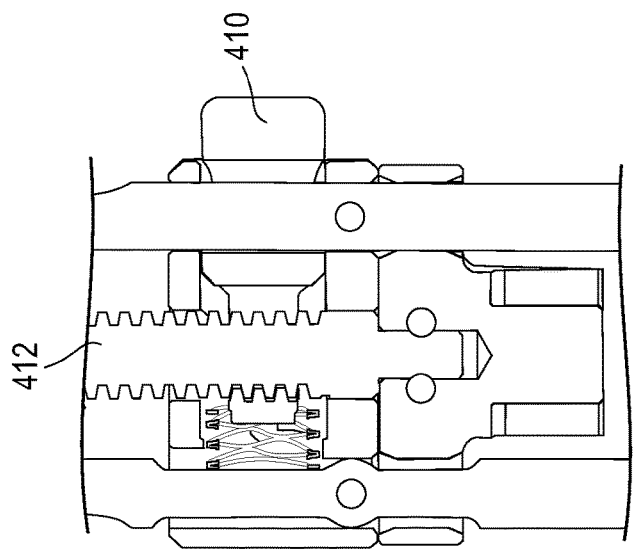
FIG. 25 is a breakaway cross section view of components of the system shown in FIG. 24.
Figure 24:
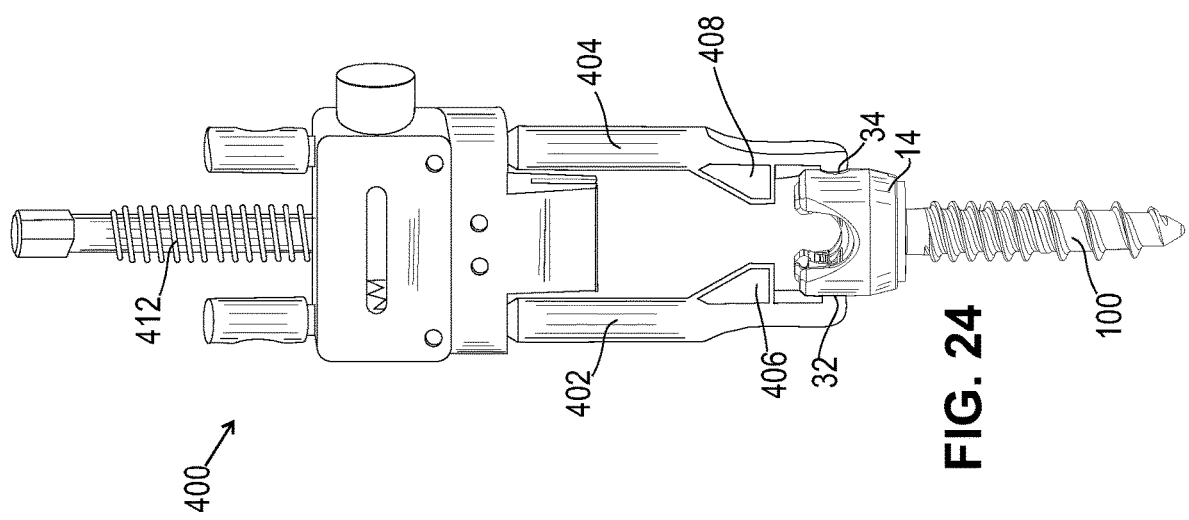
FIG. 24 is a perspective view of components of one embodiment of a spinal implant system in accordance with the principles of the present disclosure.
Figure 27:
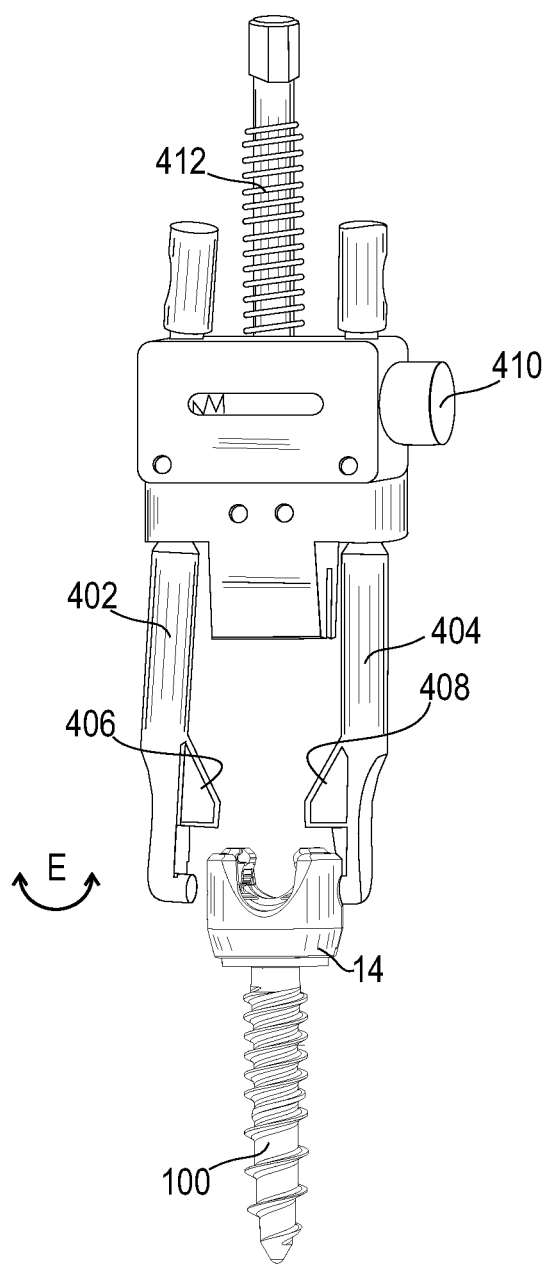
FIG. 27 is a perspective view of the components shown in FIG. 24.
Figure 28:
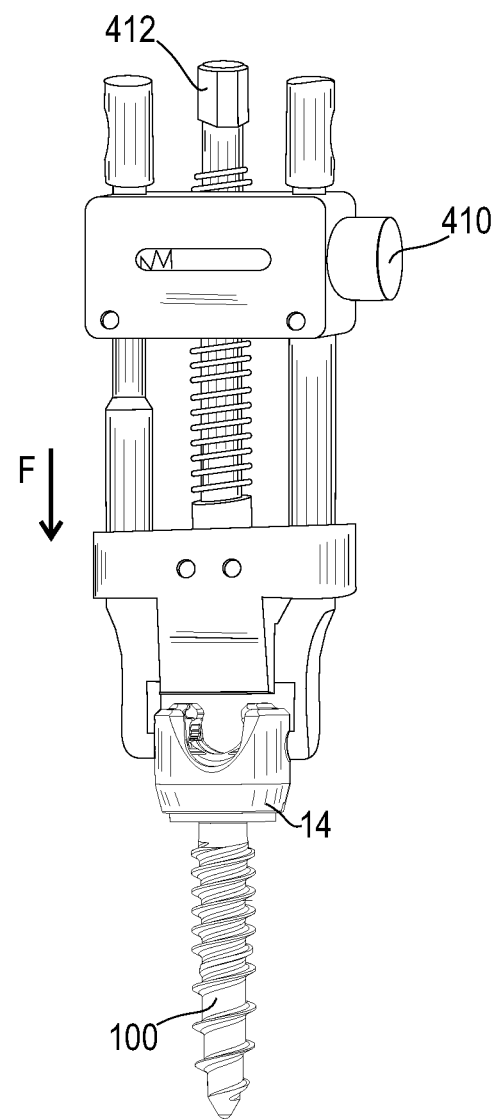
FIG. 28 is a perspective view of the components shown in FIG. 24.

Rod reducer 400 includes a pair of arms 402, 404 that engage with collar 14 via cavities 32, 34. Each arm 402, 404 is configured to pivot in a lateral direction, as shown by arrow E in FIG. 27 to connect and disconnect from collar 14. Spinal rod 18 is disposed with rod reducer 400 and ramps 406, 408 of arms 402, 404, centrally align spinal rod 18 for engagement with bone fastener 12. An actuator, for example, a quick advance button 410 is actuated to translate a threaded shaft 412 in a downward direction, as shown by arrow F in FIG. 28 to engage spinal rod 18 and translate spinal rod 18 into engagement with bone fastener 12, as shown in FIGS. 19 and 20.

One or more surfaces of spinal rod 18 engage with radial flanges 56, 58 of collect 16 and implant receiving surface 75 of crown 50. Collar 14 is translated in a direction, for example, an upward direction shown by arrow G in FIG. 22, and tapered inner surfaces 60, 62 of collar 14 engage with radial flanges 56, 58 of collet 16, rotating radial flanges 56, 58 in a direction, for example, an inward direction shown by arrows H in FIG. 23 to fix spinal rod 18 with crown 50 and collet 16.

Translation of collar 14 causes weld points 61, 63 to break. In some embodiments, force required to break weld points 61, 63 includes a force that is less than a weld strength of weld points 61, 63. In some embodiments, force applied to weld points 61, 63 includes about 6-7 Nm to generate an axial force needed to fracture weld points 61, 63 to tighten spinal rod 18 onto bone fastener 12.

In use, for treatment of a spinal disorder, bone fastener 12 including shaft 100 can be threaded and engaged with tissue. In some embodiments, bone fastener 12 is disposed adjacent vertebrae at a surgical site and is manipulated to drive, torque, insert or otherwise connect shaft 100 with vertebrae in connection with a surgical procedure, as described herein.

Figure 31:
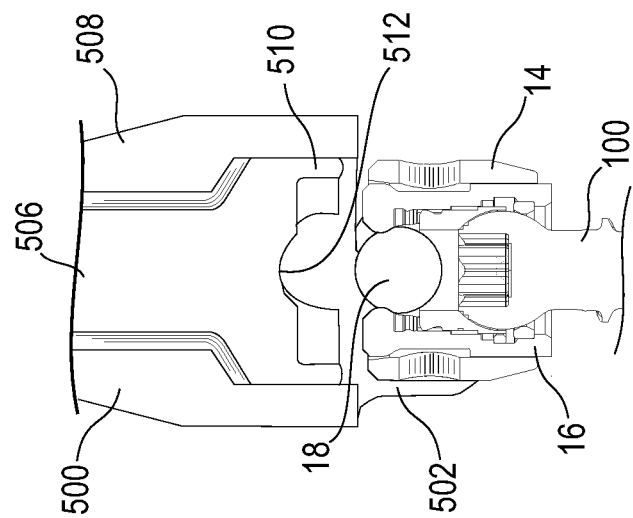
FIG. 31 is a cross section view of the components shown in FIG. 30.
Figure 30:
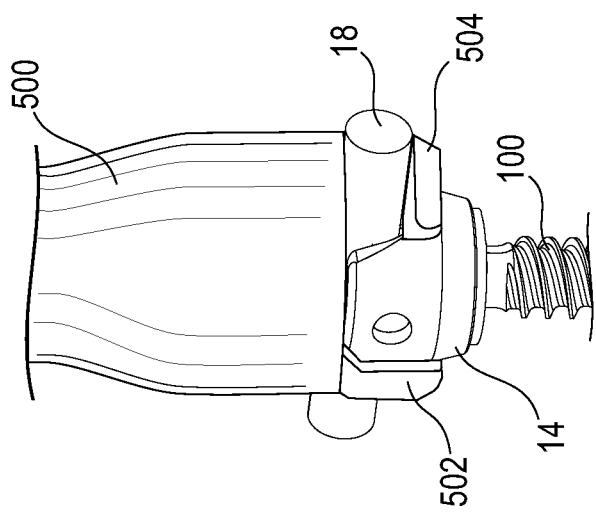
FIG. 30 is an enlarged breakaway view of the components shown in FIG. 29.
Figure 29:
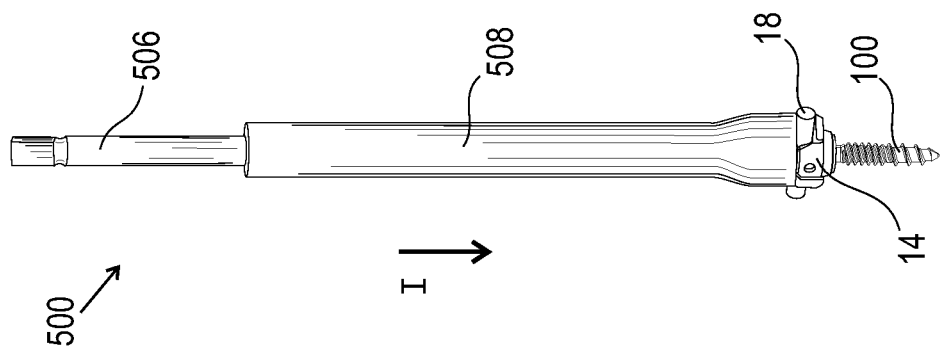
FIG. 29 is a perspective view of components of one embodiment of a spinal implant system in accordance with the principles of the present disclosure.
Figure 32:
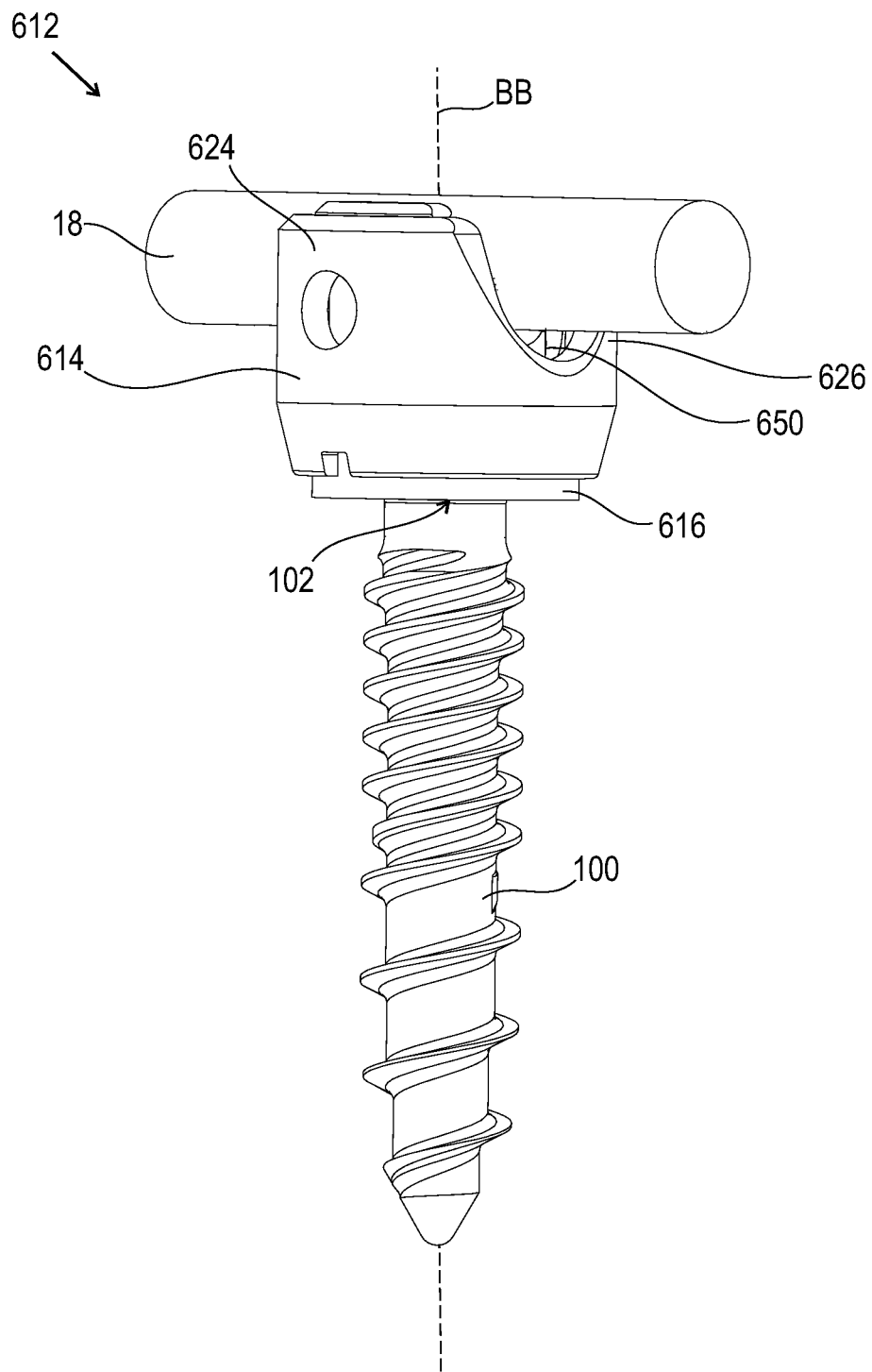
FIG. 32 is a perspective view of components of one embodiment of a spinal implant system in accordance with the principles of the present disclosure.
Figure 36:
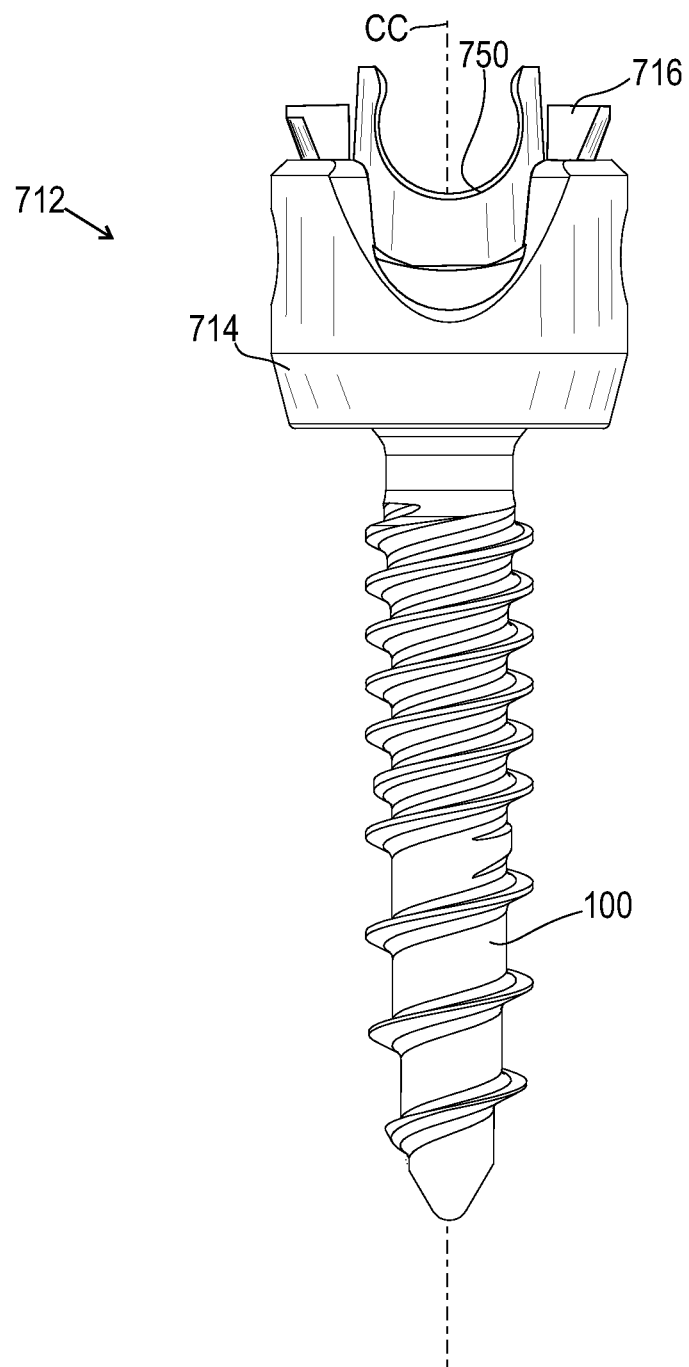
FIG. 36 is a perspective view of components of one embodiment of a spinal implant system in accordance with the principles of the present disclosure.
Figure 38:
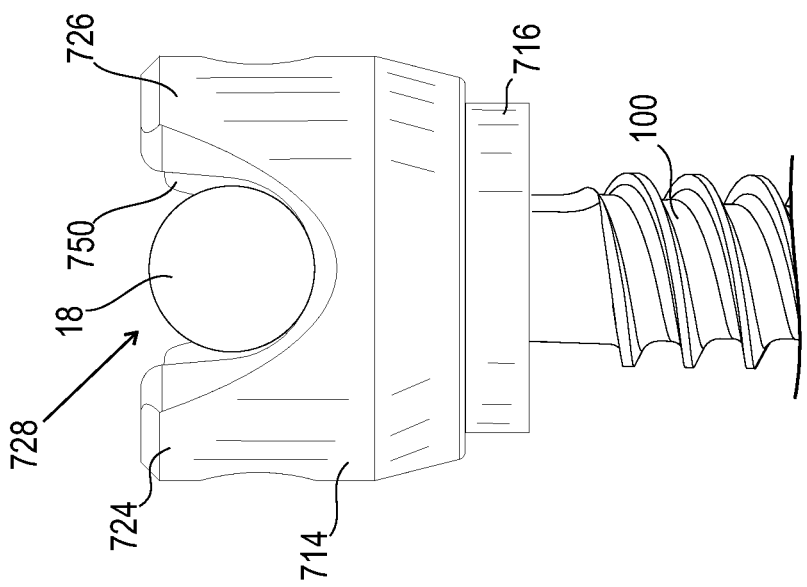
FIG. 38 is a side view of components of the system shown in FIG. 36.

As shown in FIGS. 29-31, to disengage spinal rod 18 from bone fastener 12, during a revision procedure, a surgical instrument, for example, a revision instrument 500 is employed. In some embodiments, a revision procedure is performed to adjust, modify, revise and/or correct a spinal construct from a prior surgical procedure. Revision instrument 500 is configured for connection with collar 14 and spinal rod 18. Revision instrument 500 engages with spinal rod 18 via disposing an end 502 about a portion of spinal rod 18 and tabs 504 of revision instrument 500 are rotated under spinal rod 18. An inner threaded plunger 506 is threadingly translated through an outer sleeve 508 in a direction shown by arrow I in FIG. 29, relative to spinal rod 18 to drive collar 14 in the direction shown by arrow I to disengage spinal rod 18 from bone fastener 12. As collar 14 is driven in the direction shown by arrow I, a distal portion 510 of inner threaded plunger 506 rotates such that a tip 512 contours around spinal rod 18 while pushing on collar 14.

In some embodiments, spinal implant system 10 includes an agent, which may be disposed, packed, coated or layered within, on or about the components and/or surfaces of spinal implant system 10. In some embodiments, the agent may include bone growth promoting material, for example, bone graft to enhance fixation of the fixation elements with vertebrae. In some embodiments, the agent may be HA coating. In some embodiments, the agent may include one or a plurality of therapeutic agents and/or pharmacological agents for release, including sustained release, to treat, for example, pain, inflammation and degeneration.

In some embodiments, the use of microsurgical and image guided technologies may be employed to access, view and repair spinal deterioration or damage, with the aid of spinal implant system 10. The components of spinal implant system 10 can be made of radiolucent materials such as polymers. Radiomarkers may be included for identification under x-ray, fluoroscopy, CT or other imaging techniques.

In some embodiments, spinal implant system 10 can include one or a plurality of bone fasteners 12 such as those described herein and/or fixation elements, which may be employed with a single vertebral level or a plurality of vertebral levels. In some embodiments, bone fasteners 12 may be engaged with vertebrae in various orientations, for example, series, parallel, offset, staggered and/or alternate vertebral levels. In some embodiments, bone fasteners 12 may be configured as multi-axial screws, sagittal angulation screws, pedicle screws, mono-axial screws, uni-planar screws, fixed screws, anchors, tissue penetrating screws, conventional screws, expanding screws. In some embodiments, bone fasteners 12 may be employed with wedges, anchors, buttons, clips, snaps, friction fittings, compressive fittings, expanding rivets, staples, nails, adhesives, posts, connectors, fixation plates and/or post.

In some embodiments, as shown in FIGS. 32-35, spinal implant system 10, similar to the systems and methods described herein, includes a bone fastener 612, similar to bone fastener 12. Bone fastener 612 includes a collar 614, similar to collar 14 described herein. Collar 614 is configured for engagement with a collet 616, similar to collet 16, described herein, to capture spinal rod 18 via frictional engagement, as described herein. Collar 614 includes an end 620, an end 622, and defines a longitudinal axis BB. Collar 614 includes a pair of spaced apart arms 624, 626 that define a cavity 628 therebetween configured for disposal of collet 616.

In some embodiments, arms 624, 626 each extend parallel to axis BB. Arms 624, 626 each include an arcuate outer surface extending between a pair of side surfaces. At least one of the outer surfaces and the side surfaces of arms 624, 626 may have at least one recess or cavity 632, 634 therein, configured to receive an insertion tool, compression instrument and/or instruments for inserting and tensioning bone fastener 612.

Collar 614 includes an inner surface 636 engageable with an outer surface 638 of collet 616. In some embodiments, inner surface 636 includes a tapered configuration. Inner surface 636 includes a mating surface, for example, one or more flanges 637 configured for disposal within a mating surface, for example, a groove 639 of collet 616 to fix collet 616 with collar 614. In some embodiments, the mating surfaces include a shear and/or break away feature. In some embodiments, inner surface 636 is deformable such that the mating surface engages with the mating surface of collet 616 to prevent rotation of collar 614. In some embodiments, to disengage one or more flanges 637 from groove 639, a force is required to be applied to collar 614 and collet 616. In some embodiments, collet 616 is disposed with collar 614 in a pre-assembled configuration prior to use. End 622 is configured for engagement with head 102 of shaft 100, as described herein.

Collet 616 extends between an end 640 and an end 642. End 642 is configured for connection with head 102 of shaft 100. In some embodiments, collet 616 is manually engageable with shaft 100 to connect collet 616 and shaft 100 in a non-instrumented snap-fit assembly, as described herein.

Collet 616 includes a pair of spaced apart arms 644, 646 at end 640 that define a cavity 648 therebetween configured for disposal of a crown 650, similar to crown 50, as described herein. In some embodiments, arms 644, 646 each extend parallel to axis BB. In some embodiments, arms 644, 646 are angled relative to axis BB when bone fastener 612 is in an unassembled configuration. Collar 614 is engageable with outer surface 638 of collet 616 such that arms 644, 646 are movable inwardly to frictionally engage spinal rod 18, as described herein.

Collet 616 includes outer surface 638 and an inner surface 654, and a portion of each surface 638, 654 forms arms 644, 646. Outer surface 638 of arm 644 includes a radial flange 656 and outer surface 638 of arm 646 defines a radial flange 658. Radial flanges 656, 658 are configured for engagement with tapered inner surfaces 660, 662 of collar 614, such that inner surface 654 of collet 616 frictionally engages spinal rod 18 to capture spinal rod 18 with crown 650, as described herein. In some embodiments, spinal rod 18 is disposed in a compression fit engagement with collet 616 and crown 650. In some embodiments, spinal rod 18 is disposed in a pressure fit engagement with collet 616 and crown 650.

Inner surface 654 defines a circumferential upper groove 664, similar to upper groove 64 described herein. Upper groove 664 is configured for disposal of a resilient member, for example, ring 66. Inner surface 654 defines a circumferential lower groove 668, similar to lower groove 68 described herein. Lower groove 668 is configured for disposal of a resilient member, for example, ring 70. Inner surface 654 defines an expansion groove 672, similar to expansion groove 72 described herein. Rings 66, 70 facilitate manual engagement/connection of collet 616 and shaft 100.

Collar 614 is translatable relative to collet 616 between a first, non-locking orientation and a second, locking orientation such that crown 650 frictionally engages spinal rod 18 to capture spinal rod 18 with crown 650, as described herein.

In some embodiments, as shown in FIGS. 36-39, spinal implant system 10, similar to the systems and methods described herein, includes a bone fastener 712, similar to bone fastener 612. Bone fastener 712 includes a collar 714, similar to collar 614 described herein. Collar 714 is configured for engagement with a collet 716, similar to collet 616, described herein, to capture spinal rod 18 with a crown 750, similar to crown 650, described herein, via frictional engagement, as described herein. Collar 714 includes an end 720, an end 722, and defines a longitudinal axis CC. Collar 714 includes a pair of spaced apart arms 724, 726 that define a cavity 728 therebetween configured for disposal of collet 716.

In some embodiments, arms 724, 726 each extend parallel to axis CC. Arms 724, 726 each include an arcuate outer surface extending between a pair of side surfaces. At least one of the outer surfaces and the side surfaces of arms 724, 726 may have at least one recess or cavity 732, 734 therein, configured to receive an insertion tool, compression instrument and/or instruments for inserting and tensioning bone fastener 712.

Collar 714 includes an inner surface 736 engageable with an outer surface 738 of collet 716. In some embodiments, inner surface 736 incudes a tapered configuration. Inner surface 736 includes a mating surface, for example, one or more flanges 737, similar to one or more flanges 637 described herein, configured for disposal within a mating surface, for example, a groove 739 of collet 716, similar to groove 639 described herein, to fix collet 716 with collar 714. In some embodiments, to disengage one or more flanges 737 from groove 739, a force is required to be applied to collar 714 and collet 716. In some embodiments, collet 716 is disposed with collar 714 in a pre-assembled configuration prior to use. End 722 is configured for engagement with head 102 of shaft 100.

Collet 716 extends between an end 740 and an end 742. End 742 is configured for connection with head 102 of shaft 100. In some embodiments, collet 716 is manually engageable with shaft 100 to connect collet 716 and shaft 100 in a non-instrumented snap-fit assembly, as described herein.

Collet 716 includes a pair of spaced apart arms 744, 746 at end 740 that define a cavity 748 therebetween, configured for disposal of crown 750. In some embodiments, arms 744, 746 each extend parallel to axis CC. In some embodiments, arms 744, 746 are angled relative to axis CC when bone fastener 712 is in an unassembled configuration. Collar 714 is engageable with outer surface 738 of collet 716 such that arms 744, 746 are movable inwardly to frictionally engage spinal rod 18 via crown 750, as described herein.

Collet 716 includes outer surface 738 and an inner surface 754, and a portion of each surface 738, 754 forms arms 744, 746. Outer surface 738 of arm 744 includes a tapered end 756 configuration and outer surface 738 of arm 746 defines a tapered end 758 configuration. Tapered end configurations 756, 758 are configured for engagement with tapered inner surfaces 760, 762 of collar 714, such that when arms 744, 746 move inward, inner surface 754 of collet 716 engages crown 750 to capture spinal rod 18 with crown 750, as described herein. In some embodiments, spinal rod 18 is disposed in a compression fit engagement with collet 716 and crown 750. In some embodiments, spinal rod 18 is disposed in a pressure fit engagement with collet 716 and crown 750.

Inner surface 754 defines a circumferential upper groove 764, similar to upper groove 664 described herein. Upper groove 764 is configured for disposal of a resilient member, for example, ring 66. Inner surface 754 defines a circumferential lower groove 768, similar to lower groove 668 described herein. Lower groove 768 is configured for disposal of a resilient member, for example, ring 70. Inner surface 754 defines an expansion groove 772, similar to expansion groove 672 described herein. Rings 66, 70 facilitate manual engagement/connection of collet 716 and shaft 100.

Figure 39:
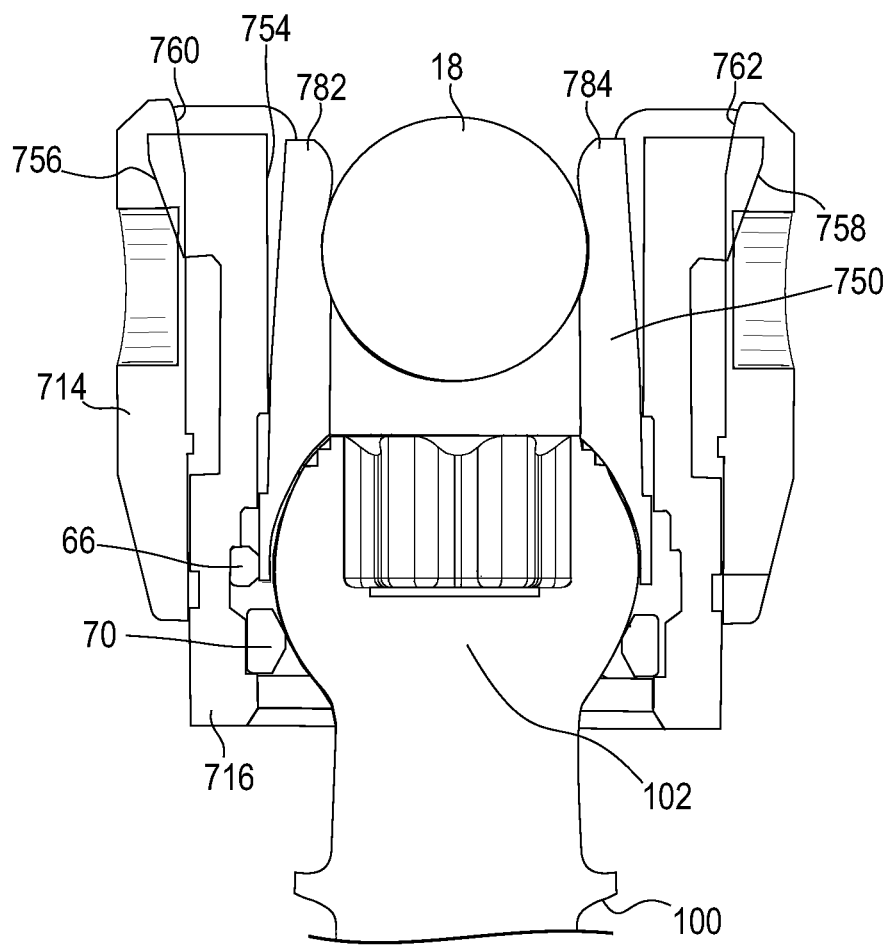
FIG. 39 is a side cross section view of components of the system shown in FIG. 38.

Crown 750 includes an end 774 and an end 776. Crown 750 is configured for disposal with collet 716 and is configured to capture spinal rod 18, as shown in FIG. 39. End 774 includes a surface that defines an implant receiving surface 775 configured for disposal with spinal rod 18. Crown 750 includes an outer surface 778 configured for engagement with collet 716, and an inner surface 780 configured for engagement with head 102 of shaft 100.

Crown 750 includes spaced apart arms 782, 784 that are movable inwardly via arms 744, 746 of collet 716 to frictionally engage spinal rod 18. In some embodiments, arms 782, 784 increase a surface area of crown 750 that engages spinal rod 18. In some embodiments, arms 782, 784 increase axial grip performance of crown 750 with spinal rod 18. In some embodiments, arms 782, 784 are angled inwardly toward axis CC.

Collar 714 is translatable relative to collet 716 between a first, non-locking orientation and a second, locking orientation, such that crown 750 via arms 782, 784 frictionally engage spinal rod 18 to capture spinal rod 18 with crown 750.

Figure 37:
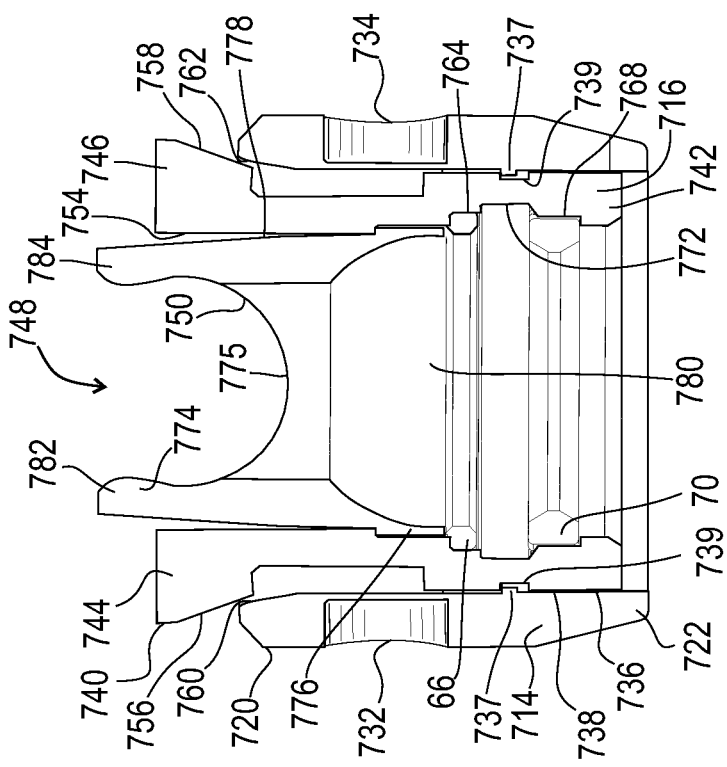
FIG. 37 is a side cross section view of components of the system shown in FIG. 36.

In the non-locking orientation, tapered end configurations 756, 758 of collet 716 do not engage with tapered inner surfaces 760, 762 of collar 714, shown in FIG. 37. In the locking orientation, collar 714 is translatable relative to collet 716 in an upward direction, such that tapered inner surfaces 760, 762 of collar 714 engage with tapered end configurations 756, 758 of collet 716, and inner surface 754 of collet 716 moves arms 782, 784 of crown 750 inwardly such that crown 750 frictionally engages spinal rod 18 to capture spinal rod 18 with crown 750.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A spinal implant comprising:
   a collar;
   a collet including an outer surface, an inner surface and spaced apart arms, the collet being connectable with a shaft; and
   a crown including a surface configured for disposal of a spinal rod,
   the collar being engageable with the outer surface such that the arms are movable inwardly such that the inner surface frictionally engages the spinal rod to capture the spinal rod with the crown.

2. A spinal implant as recited in claim 1, wherein the collet is manually engageable with the shaft to connect the collet and the shaft in a non-instrumented snap-fit assembly.

3. A spinal implant as recited in claim 1, wherein the collet includes a first groove configured for disposal of a first resilient member that is contractable in the first groove, and a second groove configured for disposal of a second resilient member that is expandable in the second groove to connect the collet and the shaft.

4. A spinal implant as recited in claim 1, wherein the collar is engageable with the outer surface such that the inner surface frictionally engages the spinal rod to capture the spinal rod with the crown.

5. A spinal implant as recited in claim 4, wherein the collar includes an inner surface engageable with the outer surface, at least one of the inner surface of the collar and the outer surface of the collet including a tapered configuration.

6. A spinal implant as recited in claim 1, wherein the collar includes a tapered inner surface and the outer surface includes a projection, the tapered inner surface being engageable with the projection such that the inner surface of the collet frictionally engages the spinal rod to capture the spinal rod with the crown.

7. A spinal implant as recited in claim 1, wherein the collar includes a flange disposed within a groove of the collet to fix the collet with the collar.

8. A spinal implant as recited in claim 1, wherein the collar is translatable relative to the collet between a first orientation and a second, locking orientation such that the collar is engaged with the outer surface and the inner surface frictionally engages the spinal rod to capture the spinal rod with the crown.

9. A spinal implant system comprising:
   a spinal rod;
   a bone fastener including
   a collar,
   a collet including an outer surface, an inner surface and spaced apart arms,
   a crown, and
   a shaft connectable with the collet,
   the collar being engageable with the outer surface such that the arms are movable inwardly such that the inner surface frictionally engages the spinal rod to capture the spinal rod with the crown; and
   a surgical instrument engageable with the bone fastener.

10. A spinal implant as recited in claim 9, wherein the surgical instrument includes an inserter connectable with the collet.

11. A spinal implant as recited in claim 9, wherein the surgical instrument includes a rod reducer connectable with the collar.

12. A spinal implant as recited in claim 9, wherein the surgical instrument includes a revision instrument connectable with the collar and the spinal rod.

13. A spinal implant as recited in claim 9, wherein the collet is manually engageable with the shaft to connect the collet and the shaft in a non-instrumented snap-fit assembly.

14. A spinal implant comprising:
   a collar;
   a collet including an inner surface, a first groove and a second groove, the collet being connectable with a shaft; and
   a crown including an inner surface and an outer surface,
   the collar being engageable with the collet such that the inner surface of the collet engages the outer surface of the crown such that the inner surface of the crown is frictionally engageable with a spinal rod to capture the spinal rod with the crown,
   the first groove configured for disposal of a first resilient member that is contractable in the first groove, and the second groove configured for disposal of a second resilient member that is expandable in the second groove to connect the collet and the shaft.

15. A spinal implant as recited in claim 14, wherein the collet is manually engageable with the shaft to connect the collet and the shaft in a non-instrumented snap-fit assembly.

16. A spinal implant as recited in claim 14, wherein the collar includes a tapered inner surface and the collet includes a tapered outer surface, the tapered inner surface being engageable with the tapered outer surface such that the inner surface of the crown frictionally engages the spinal rod to capture the spinal rod with the crown.

17. A spinal implant as recited in claim 14, wherein the crown includes spaced apart arms movable inwardly to frictionally engage the spinal rod.

18. A spinal implant as recited in claim 14, wherein the collar is translatable relative to the collet between a first orientation and a second, locking orientation such that the inner surface of the crown frictionally engages the spinal rod to capture the spinal rod with the crown.

* * * * *